US011155688B2

United States Patent
Topolkaraev et al.

(10) Patent No.: US 11,155,688 B2
(45) Date of Patent: *Oct. 26, 2021

(54) POLYOLEFIN MATERIAL HAVING A LOW DENSITY

(71) Applicant: Kimberly-Clark Worldwide, Inc., Neenah, WI (US)

(72) Inventors: Vasily A. Topolkaraev, Appleton, WI (US); Ryan J. McEneany, Appleton, WI (US); Antonio J. Carrillo, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 728 days.

This patent is subject to a terminal disclaimer.

(21) Appl. No.: 14/895,054

(22) PCT Filed: Jun. 6, 2014

(86) PCT No.: PCT/IB2014/062015
§ 371 (c)(1),
(2) Date: Dec. 1, 2015

(87) PCT Pub. No.: WO2014/199268
PCT Pub. Date: Dec. 18, 2014

(65) Prior Publication Data
US 2016/0115291 A1    Apr. 28, 2016

Related U.S. Application Data

(60) Provisional application No. 61/907,572, filed on Nov. 22, 2013, provisional application No. 61/833,980, filed on Jun. 12, 2013.

(51) Int. Cl.
*C08J 9/00*    (2006.01)
*C08J 5/18*    (2006.01)
(Continued)

(52) U.S. Cl.
CPC ............. *C08J 9/0061* (2013.01); *A61F 13/53* (2013.01); *A61L 15/225* (2013.01); *A61L 15/24* (2013.01);
(Continued)

(58) Field of Classification Search
CPC .... B01D 67/0067; B01D 71/26; C08J 9/0071; C08J 9/0061; C08J 2323/10–14;
(Continued)

(56) References Cited

U.S. PATENT DOCUMENTS 3,354,506 A    11/1967  Raley
3,423,255 A     1/1969  Joyce
(Continued)

FOREIGN PATENT DOCUMENTS

CN    101316708    12/2008
CN    102782027    11/2012
(Continued)

OTHER PUBLICATIONS

ANTEC 2012 Plastics: Annual Technical Conference Proceedings. Society of Plastics Engineers, 2012.*
(Continued)

*Primary Examiner* — Jennifer A Gillett
(74) *Attorney, Agent, or Firm* — Dority & Manning, P.A.

(57) ABSTRACT

A polyolefin material that is formed by solid state drawing of a thermoplastic composition containing a continuous phase that includes a polyolefin matrix polymer and nanoinclusion additive is provided. The nanoinclusion additive is dispersed within the continuous phase as discrete nano-scale phase domains. When drawn, the nano-scale phase domains are able to interact with the matrix in a unique manner to create a network of nanopores.

31 Claims, 14 Drawing Sheets

(51) Int. Cl.

| | |
|---|---|
| *C08L 23/02* | (2006.01) |
| *B01D 71/26* | (2006.01) |
| *B01D 67/00* | (2006.01) |
| *C08L 67/00* | (2006.01) |
| *C08L 23/08* | (2006.01) |
| *D01F 1/10* | (2006.01) |
| *D01F 1/08* | (2006.01) |
| *D01F 6/06* | (2006.01) |
| *D01D 5/247* | (2006.01) |
| *D01F 6/46* | (2006.01) |
| *A61F 13/53* | (2006.01) |
| *A61L 15/22* | (2006.01) |
| *A61L 15/24* | (2006.01) |
| *A61L 15/42* | (2006.01) |
| *B29C 55/00* | (2006.01) |
| *B32B 3/26* | (2006.01) |
| *B32B 5/02* | (2006.01) |
| *B32B 27/32* | (2006.01) |
| *C08J 9/28* | (2006.01) |
| *B29C 55/14* | (2006.01) |
| *B29C 55/20* | (2006.01) |
| *B32B 27/20* | (2006.01) |
| *C08L 23/12* | (2006.01) |
| *B29K 105/16* | (2006.01) |
| *B29K 23/00* | (2006.01) |
| *B29K 105/04* | (2006.01) |
| *A61F 13/514* | (2006.01) |
| *A61F 13/511* | (2006.01) |
| *B29K 63/00* | (2006.01) |
| *B29L 7/00* | (2006.01) |

(52) U.S. Cl.
CPC ........ *A61L 15/425* (2013.01); *B01D 67/0027* (2013.01); *B01D 71/26* (2013.01); *B29C 55/005* (2013.01); *B29C 55/14* (2013.01); *B29C 55/20* (2013.01); *B32B 3/26* (2013.01); *B32B 5/022* (2013.01); *B32B 27/205* (2013.01); *B32B 27/32* (2013.01); *C08J 5/18* (2013.01); *C08J 9/0023* (2013.01); *C08J 9/0095* (2013.01); *C08J 9/28* (2013.01); *C08L 23/02* (2013.01); *C08L 23/0815* (2013.01); *C08L 23/0884* (2013.01); *C08L 23/12* (2013.01); *C08L 67/00* (2013.01); *D01D 5/247* (2013.01); *D01F 1/08* (2013.01); *D01F 1/10* (2013.01); *D01F 6/06* (2013.01); *D01F 6/46* (2013.01); *A61F 2013/51147* (2013.01); *A61F 2013/51411* (2013.01); *A61F 2013/51413* (2013.01); *A61F 2013/51415* (2013.01); *B29K 2023/00* (2013.01); *B29K 2023/12* (2013.01); *B29K 2063/00* (2013.01); *B29K 2105/041* (2013.01); *B29K 2105/162* (2013.01); *B29L 2007/007* (2013.01); *B32B 2264/0235* (2013.01); *B32B 2264/0278* (2013.01); *B32B 2307/726* (2013.01); *B32B 2307/7265* (2013.01); *B32B 2432/00* (2013.01); *B32B 2439/70* (2013.01); *B32B 2555/02* (2013.01); *C08J 2201/02* (2013.01); *C08J 2201/0522* (2013.01); *C08J 2205/042* (2013.01); *C08J 2323/06* (2013.01); *C08J 2323/08* (2013.01); *C08J 2323/12* (2013.01); *C08J 2423/08* (2013.01); *C08J 2433/10* (2013.01); *C08J 2433/14* (2013.01); *C08J 2467/04* (2013.01); *C08L 2205/03* (2013.01)

(58) Field of Classification Search
CPC ....... C08J 5/18; C08J 9/0095; C08L 23/0815; C08L 23/12; C08L 23/14; C08L 23/02; C08L 67/00; C08L 23/0884; D01D 5/247; B32B 27/205; B32B 3/26; B32B 27/32; B32B 2264/0235; B32B 2264/0278; B32B 2439/70; B32B 2307/726; B32B 2307/7265; B32B 2432/00; B32B 2555/02
USPC .................................. 442/339, 372
See application file for complete search history.

(56) References Cited

U.S. PATENT DOCUMENTS

| | | | |
|---|---|---|---|
| 3,650,649 | A | 3/1972 | Schippers |
| 3,801,429 | A | 4/1974 | Schrenk et al. |
| 3,802,817 | A | 4/1974 | Matsuki et al. |
| 3,855,046 | A | 12/1974 | Hansen et al. |
| 4,041,203 | A | 8/1977 | Brock et al. |
| 4,100,324 | A | 7/1978 | Anderson et al. |
| 4,282,735 | A | 8/1981 | Break |
| 4,374,888 | A | 2/1983 | Bomslaeger |
| 4,557,132 | A | 12/1985 | Break |
| 4,698,372 | A | 10/1987 | Moss |
| 4,704,116 | A | 11/1987 | Enloe |
| 4,758,462 | A * | 7/1988 | Park .............. B32B 27/20 428/213 |
| 4,766,029 | A | 8/1988 | Brock et al. |
| 4,797,468 | A | 1/1989 | De Vries |
| 4,798,603 | A | 1/1989 | Meyer et al. |
| 4,801,494 | A | 1/1989 | Datta et al. |
| 4,902,553 | A | 2/1990 | Hwang et al. |
| 4,908,026 | A | 3/1990 | Sukiennik et al. |
| 4,937,299 | A | 6/1990 | Ewen et al. |
| D315,990 | S | 4/1991 | Blenke et al. |
| 5,169,706 | A | 12/1992 | Collier, IV et al. |
| 5,179,164 | A | 1/1993 | Lausberg et al. |
| 5,186,835 | A * | 2/1993 | Masuoka .......... B01D 67/0093 210/500.36 |
| 5,192,606 | A | 3/1993 | Proxmire et al. |
| 5,213,881 | A | 5/1993 | Timmons et al. |
| 5,218,071 | A | 6/1993 | Tsutsui et al. |
| 5,238,735 | A | 8/1993 | Nagou et al. |
| 5,248,309 | A | 9/1993 | Serbiak et al. |
| 5,272,236 | A | 12/1993 | Lai et al. |
| 5,278,272 | A | 1/1994 | Lai et al. |
| 5,284,309 | A | 2/1994 | Salvatore et al. |
| 5,284,703 | A | 2/1994 | Everhart et al. |
| 5,322,728 | A | 6/1994 | Davey et al. |
| 5,350,624 | A | 9/1994 | Georger et al. |
| D358,035 | S | 5/1995 | Zander et al. |
| 5,464,688 | A | 11/1995 | Timmons et al. |
| 5,470,944 | A | 11/1995 | Bonsignore |
| 5,472,775 | A | 12/1995 | Obijeski et al. |
| 5,486,166 | A | 1/1996 | Bishop et al. |
| 5,490,846 | A | 2/1996 | Ellis et al. |
| 5,539,056 | A | 7/1996 | Yang et al. |
| 5,571,619 | A | 11/1996 | McAlpin et al. |
| 5,596,052 | A | 1/1997 | Resconi et al. |
| 5,620,779 | A | 4/1997 | Levy et al. |
| D384,508 | S | 10/1997 | Zander et al. |
| D384,819 | S | 10/1997 | Zander et al. |
| 5,702,377 | A | 12/1997 | Collier, IV et al. |
| D390,708 | S | 2/1998 | Brown |
| 5,766,760 | A | 6/1998 | Tsai et al. |
| 5,770,682 | A | 6/1998 | Ohara et al. |
| 5,821,327 | A | 10/1998 | Oota et al. |
| 5,843,057 | A | 12/1998 | McCormack |
| 5,855,999 | A | 1/1999 | McCormack |
| 5,880,254 | A | 3/1999 | Ohara et al. |
| 5,931,823 | A | 8/1999 | Stokes et al. |
| 5,932,497 | A | 8/1999 | Morman et al. |
| 5,962,112 | A | 10/1999 | Haynes et al. |
| 5,968,643 | A | 10/1999 | Topolkaraev et al. |
| 5,997,981 | A | 12/1999 | McCormack |
| 6,002,064 | A | 12/1999 | Kobylivker et al. |
| D418,305 | S | 1/2000 | Zander et al. |

(56) References Cited

U.S. PATENT DOCUMENTS

| | | | |
|---|---|---|---|
| 6,015,764 | A | 1/2000 | McCormack et al. |
| 6,037,033 | A | 3/2000 | Hunter |
| 6,037,281 | A | 3/2000 | Mathis et al. |
| 6,060,638 | A | 5/2000 | Paul et al. |
| 6,071,451 | A | 6/2000 | Wang et al. |
| D428,267 | S | 7/2000 | Romano, III et al. |
| 6,090,325 | A | 7/2000 | Wheat et al. |
| 6,093,665 | A | 7/2000 | Sayovitz et al. |
| 6,096,014 | A | 8/2000 | Haffner et al. |
| 6,111,163 | A | 8/2000 | McCormack et al. |
| 6,150,002 | A | 11/2000 | Varona |
| 6,214,933 | B1 | 4/2001 | Wang et al. |
| 6,268,048 | B1 | 7/2001 | Topolkaraev et al. |
| 6,326,458 | B1 | 12/2001 | Gruber et al. |
| 6,380,445 | B1 | 4/2002 | Rietz et al. |
| 6,389,864 | B1 | 5/2002 | Chubb et al. |
| 6,461,457 | B1 | 10/2002 | Taylor et al. |
| 6,485,446 | B1 | 11/2002 | Brother et al. |
| 6,500,563 | B1 | 12/2002 | Datta et al. |
| 6,582,810 | B2 | 6/2003 | Heffelfinger |
| 6,586,073 | B2 | 7/2003 | Perez et al. |
| 6,642,429 | B1 | 11/2003 | Carter et al. |
| 6,663,611 | B2 | 12/2003 | Blaney et al. |
| 6,716,203 | B2 | 4/2004 | Sorebo et al. |
| 6,824,680 | B2 | 11/2004 | Chandavasu et al. |
| 6,824,734 | B2 | 11/2004 | Boggs et al. |
| 7,060,867 | B2 | 6/2006 | Jameson |
| 7,097,904 | B2 | 8/2006 | Ochi et al. |
| 7,141,168 | B2 | 11/2006 | Sakamoto et al. |
| 7,341,776 | B1 | 3/2008 | Milliren et al. |
| 7,984,591 | B2 | 7/2011 | Cashin et al. |
| 7,998,579 | B2 | 8/2011 | Lin et al. |
| 8,105,682 | B2 | 1/2012 | Sun et al. |
| 8,268,738 | B2 | 9/2012 | McEneany et al. |
| 8,313,818 | B2 | 11/2012 | Vo et al. |
| 8,323,837 | B2 | 12/2012 | Nishida et al. |
| 8,334,327 | B2 | 12/2012 | Kaufman et al. |
| 8,362,145 | B2 | 1/2013 | Li et al. |
| 8,603,614 | B2 | 12/2013 | Lam et al. |
| 8,936,740 | B2 | 1/2015 | Topolkaraev et al. |
| 9,067,392 | B2 | 6/2015 | Mohr et al. |
| 2002/0180082 | A1* | 12/2002 | Chandavasu ........... B29C 48/08 264/41 |
| 2003/0116462 | A1 | 6/2003 | Sorebo et al. |
| 2004/0002273 | A1 | 1/2004 | Fitting et al. |
| 2005/0054255 | A1 | 3/2005 | Morman et al. |
| 2005/0059941 | A1 | 3/2005 | Baldwin et al. |
| 2005/0245162 | A1 | 11/2005 | McCormack et al. |
| 2008/0311320 | A1* | 12/2008 | Hiruma ................... B32B 27/08 428/34.9 |
| 2009/0008816 | A1 | 1/2009 | Takita et al. |
| 2009/0318884 | A1 | 12/2009 | Meyer et al. |
| 2009/0326130 | A1* | 12/2009 | Li .............................. C08J 5/18 524/423 |
| 2010/0068471 | A1 | 3/2010 | Lubart et al. |
| 2010/0068484 | A1* | 3/2010 | Kaufman ................... C08J 5/18 428/212 |
| 2010/0305529 | A1 | 12/2010 | Ashton et al. |
| 2010/0313507 | A1 | 12/2010 | Castro et al. |
| 2011/0091714 | A1 | 4/2011 | Chen et al. |
| 2011/0183563 | A1 | 7/2011 | Ochi et al. |
| 2011/0252739 | A1 | 10/2011 | Leeser et al. |
| 2011/0256346 | A1 | 10/2011 | Bowden et al. |
| 2012/0040185 | A1 | 2/2012 | Topolkaraev et al. |
| 2012/0109090 | A1 | 5/2012 | Reichardt et al. |
| 2012/0225272 | A1 | 9/2012 | Costeux et al. |
| 2012/0231242 | A1 | 9/2012 | Boyer et al. |
| 2013/0118981 | A1* | 5/2013 | Vogel ..................... B01D 69/08 210/650 |
| 2014/0044954 | A1 | 2/2014 | Matsubara et al. |
| 2014/0170922 | A1 | 6/2014 | Poruthoor et al. |
| 2016/0177048 | A1 | 6/2016 | Topolkaraev et al. |
| 2016/0185929 | A1 | 6/2016 | Topolkaraev et al. |

FOREIGN PATENT DOCUMENTS

| | | | |
|---|---|---|---|
| EP | 0348887 | A2 | 1/1990 |
| EP | 0348887 | A3 | 1/1990 |
| EP | 0609881 | A1 | 8/1994 |
| EP | 0609881 | B1 | 8/1999 |
| EP | 1152025 | A1 | 11/2001 |
| EP | 1152025 | A4 | 11/2001 |
| EP | 1695995 | | 8/2006 |
| EP | 2233524 | | 9/2010 |
| JP | 2008144039 | A * | 6/2008 |
| WO | WO 99/32272 | A1 | 7/1999 |
| WO | WO02085969 | | 10/2002 |
| WO | WO2009/152021 | A2 | 12/2009 |
| WO | WO2009/152021 | A3 | 12/2009 |
| WO | WO-2012013345 | A1 * | 2/2012 ............ B01D 69/08 |
| WO | WO2013066487 | | 5/2013 |
| WO | WO2013118021 | | 8/2013 |
| WO | WO2014/199269 | | 12/2014 |
| WO | WO2014/199270 | | 12/2014 |
| WO | WO2014/199271 | | 12/2014 |
| WO | WO2014/199272 | | 12/2014 |
| WO | WO2014/199273 | | 12/2014 |
| WO | WO2014/199274 | | 12/2014 |
| WO | WO2014/199275 | | 12/2014 |
| WO | WO2014/199276 | | 12/2014 |
| WO | WO2014/199277 | | 12/2014 |
| WO | WO2014/199278 | | 12/2014 |
| WO | WO2014/199279 | | 12/2014 |

OTHER PUBLICATIONS

Liu, Zengshe Kraus, George. (2015). Green Materials from Plant Oils. Royal Society of Chemistry.*

Krevelen, D.W. van Nijenhuis, K. te. (2009). Properties of Polymers—Their Correlation with Chemical Structure; Their Numerical Estimation and Prediction from Additive Group Contributions (4th, Completely Revised Edition). Elsevier.*

JP 2008144039 English Machine Translation, Espacenet, tranlsated Dec. 20, 2017.*

Diameter, Define Diameter, www.dictionary.com/browse/diameter, retrieced Sep. 17, 2018.*

Poly(butylene terephthalate), PolymerProcessing.com, www.polymerproessing.com/polymers/PBT.html, retreived Aug. 31, 2020.*

Polyester Typical Properties Generic PBT, Prospector, https://plastics.ulprospector.com/generics/37/c/t/polyester-properties-process, retrieved Aug. 31, 2020.*

Kutz, Myer. (2015). Mechanical Engineers' Handbook, vol. 1—Materials and Engineering Mechanics (4th Edition). John Wiley & Sons.*

National Center for Biotechnology Information. PubChem Compound Summary for CID 26042, Titanium dioxide, https://pubchem.ncbi.nlm.nih.gov/compound/Titanium-dioxide. Accessed Aug. 31, 2020.*

European Search Report dated Dec. 15, 2016, 4 pages.

Abstract of Japanese Patent—JP2000226725, Aug. 15, 2000, 1 page.

Abstract of Japanese Patent—JP2008144039, Jun. 26, 2008, 2 pages.

State Intellectual Property Office of China Search Report, dated Oct. 26, 2017, 3 pages.

Karst et al., "Using the solubility parameter to explain disperse dye sorption on polylactide".

Lee et al., "Development of Discrete Nanopores I: Tension of Polypropylene/Polyethylene Copolymer Blends," *Journal of Applied Polymer Science*, vol. 91, No. 6, Mar. 15, 2004, pp. 3462-3650.

International Search Report and Written Opinion for PCT/IB2014/062015 dated Sep. 23, 2014, 13 pages.

* cited by examiner

POLYOLEFIN MATERIAL HAVING A LOW DENSITY

RELATED APPLICATION

The present application is the national stage entry of International Patent. Application No. PCT/IB2014/062015 having filing date of Jun. 6, 2014 which claims priority to U.S. provisional applications Ser. No. 61/833,980, filed on Jun. 12, 2013, and 61/907,566, on filed Nov. 22, 2013, which are incorporated herein in their entirety by reference thereto.

BACKGROUND OF THE INVENTION

Significant efforts have been made to produce low density polyolefin materials to improve the use of natural resources and reduction of the carbon footprint in finished products. A typical approach to producing low density polyolefin materials is by foaming the polymer using physical or chemical blowing agents, which create gas cells though the bulk. Chemical blowing agents are compounds that undergo chemical reaction liberating gas that creates the cellular structure through the bulk of the polymer. Physical blowing agents are typically compressed gases that are dispersed in the polymer and expand creating the cells. Regardless, typical foaming processes induce low molecular orientation because the cell formation happens when the polymer is in the molten state. This prevents the polymer from strain hardening, which typically occurs at temperatures well above the melting temperature or glass transition temperature of the polymer, yielding products with low mechanical strength. Furthermore, typical foaming processes generate large cell sizes, such as greater than 100 μm. This reduces the melt strength, thus leading to breaks in high speed production processes with high deformation rates (e.g., fiber spinning, film formation, molding, etc.).

As such, a need currently exists for an improved technique in forming low density polyolefin materials.

SUMMARY OF THE INVENTION

In accordance with one embodiment of the present invention, a polyolefin material is disclosed that is formed by drawing of a thermoplastic composition containing a continuous phase that includes a polyolefin matrix polymer, wherein a nanoinclusion additive is dispersed within the continuous phase in the form of discrete domains. A porous network is defined in the composition that includes a plurality of nanopores having an average cross-sectional dimension of about 800 nanometers or less. The composition has a density of about 0.90 g/cm$^3$ or less.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF REPRESENTATIVE EMBODIMENTS

Figure 1:
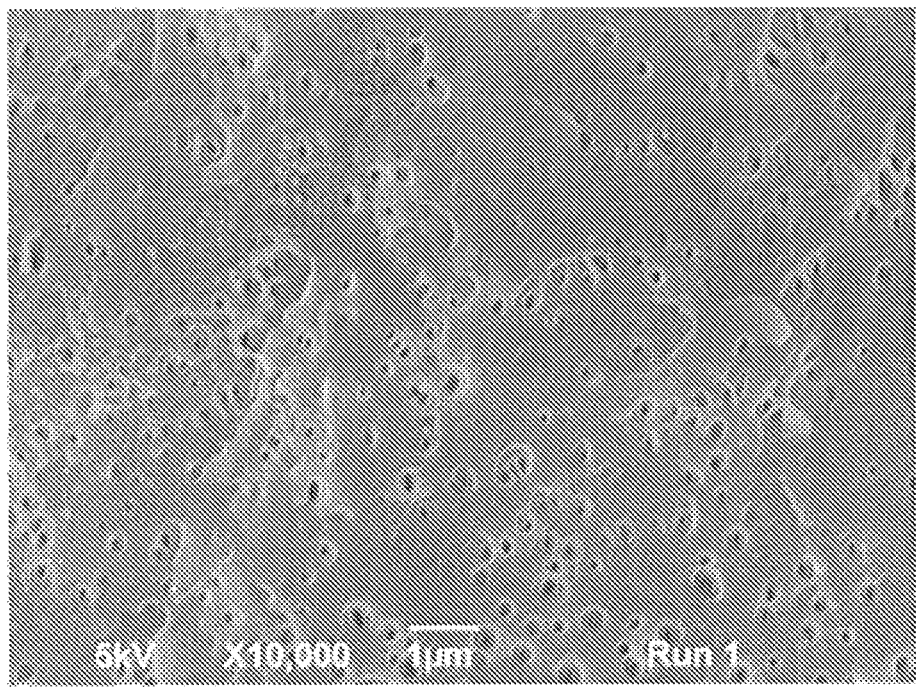
FIG. 1 is an SEM photomicrograph of the unstretched injection molded sample of Example 1 (polypropylene and alkoxylated alcohol) after freeze fracturing in liquid nitrogen.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a polyolefin material (e.g., film, fibrous material, molded article, etc.) that is formed by drawing of a thermoplastic composition (e.g., solid state drawing) containing a continuous phase that includes a polyolefin matrix polymer. The composition also contains a nanoinclusion additive that is at least partially incompatible with the polyolefin matrix polymer so that it becomes dispersed within the continuous phase as discrete nano-scale phase domains. During drawing, when the composition is subjected to a deformation and elongational strain, the present inventors have discovered that these nano-scale phase domains are able to interact in a unique manner to create a network of pores. Namely, it is believed that elongational strain can initiate intensive localized shear zones and/or stress intensity zones (e.g., normal stresses) near the discrete phase domains as a result of stress concentrations that arise from the incompatibility of the materials. These shear and/or stress intensity zones cause some initial debonding in the polyolefin matrix adjacent to the domains. Once initial pores are formed, the matrix located between domains can deform plastically to create internal stretched areas that locally narrow (or neck) and strain-harden. This process allows the formation of pores through the bulk of the composition that grow in the stretching direction, thereby leading to the formation of a porous network while the molecular orientation leads to strain-hardening that enhances mechanical strength.

Through the techniques noted above, a unique porous network may be formed in the polyolefin material so that the average percent volume occupied by the pores within a given unit volume of the material may be from about 15% to about 80% per $cm^3$, in some embodiments from about 20% to about 70%, and in some embodiments, from about 30% to about 60% per cubic centimeter of the material. With such a pore volume, the composition may have a relatively low density, such as about 0.90 grams per cubic centimeter ("$g/cm^3$") or less, in some embodiments about 0.85 $g/cm^3$ or less, in some embodiments about 0.80 $g/cm^3$ or less, in some embodiments from about 0.10 $g/cm^3$ to about 0.75 $g/cm^3$, and in some embodiments, from about 0.20 $g/cm^3$ to about 0.70 $g/cm^3$. A substantial portion of pores in the porous network are also of a "nano-scale" size ("nanopores"), such as those having an average cross-sectional dimension of about 800 nanometers or less, in some embodiments from about 5 to about 700 nanometers, and in some embodiments, from about 10 to about 500 nanometers. The term "cross-sectional dimension" generally refers to a characteristic dimension (e.g., width or diameter) of a pore, which is substantially orthogonal to its major axis (e.g., length) and also typically substantially orthogonal to the direction of the stress applied during drawing. The nanopores may also have an average axial dimension within the range of from about 100 to about 5000 nanometers, in some embodiments from about 50 to about 2000 nanometers, and in some embodiments, from about 100 to about 1000 nanometers. The "axial dimension" is the dimension in the direction of the major axis (e.g., length), which is typically in the direction of drawing. Such nanopores may, for example, constitute about 15 vol. % or more, in some embodiments about 20 vol. % or more, in some embodiments from about 30 vol. % to 100 vol. %, and in some embodiments, from about 40 vol. % to about 90 vol. % of the total pore volume in the polyolefin material.

Besides a reduced density, the nanoporous structure may also provide a variety of additional different benefits to the resulting polyolefin material. For example, such a structure can help restrict the flow of fluids through the material and be generally impermeable to fluids (e.g., liquid water), thereby allowing the material to insulate a surface from water penetration. In this regard, the polyolefin material may have a relatively high hydrohead value of about 50 centimeters ("cm") or more, in some embodiments about 100 cm or more, in some embodiments, about 150 cm or more, and in some embodiments, from about 200 cm to about 1000 cm, as determined in accordance with ATTCC 127-2008. Other beneficial properties may also be achieved. For example, the resulting polyolefin material may be generally permeable to water vapors. The permeability of the material to water vapor may characterized by its relatively high water vapor transmission rate ("WVTR"), which is the rate at which water vapor permeates through a material as measured in units of grams per meter squared per 24 hours ($g/m^2/24$ hrs). For example, the polyolefin material may exhibit a WVTR of about 300 $g/m^2$-24 hours or more, in some embodiments about 500 $g/m^2$-24 hours or more, in some embodiments about 1,000 $g/m^2$-24 hours or more, and in some embodiments, from about 3,000 to about 15,000 $g/m^2$-24 hours, such as determined in accordance with ASTM E96/96M-12, Procedure B or INDA Test Procedure IST-70.4 (01). The polyolefin material can also act as a thermal barrier that exhibits a relatively low thermal conductivity, such as about 0.40 watts per meter-kelvin ("W/m-K") or less, in some embodiments about 0.20 W/m-K or less, in some embodiments about 0.15 W/m-K or less, in some embodiments from about 0.01 to about 0.12 W/m-K, and in some embodiments, from about 0.02 to about 0.10 W/m-K. Notably, the material is capable of achieving such low thermal conductivity values at relatively low thicknesses, which can allow the material to possess a greater degree of flexibility and conformability, as well as reduce the space it occupies in an article. For this reason, the polyolefin material may also exhibit a relatively low "thermal admittance", which is equal to the thermal conductivity of the material divided by its thickness and is provided in units of watts per square meter-kelvins ("$W/m^2K$"). For example, the material may exhibit a thermal admittance of about 1000 $W/m^2K$ or less, in some embodiments from about 10 to about 800 $W/m^2K$, in some embodiments from about 20 to about 500 $W/m^2K$, and in some embodiments, from about 40 to about 200 $W/m^2K$. The actual thickness of the polyolefin material may depend on its particular form, but typically ranges from about 5 micrometers to about 100 millimeters, in some embodiments from about 10 micrometers to about 50 millimeters, in some embodiments from about 200 micrometers to about 25 millimeters.

Various embodiments of the present invention will now be described in more detail.

I. Thermoplastic Composition

A. Polyolefin Matrix

Polyolefins typically constitute from about 60 wt. % to about 99 wt. %, in some embodiments from about 60 wt. % to about 98 wt. %, and in some embodiments, from about 80 wt. % to about 95 wt. % of the thermoplastic composition. The polyolefin may have a melting temperature of from about 100° C. to about 220° C., in some embodiments from about 120° C. to about 200° C., and in some embodiments, from about 140° C. to about 1800° C. The melting temperature may be determined using differential scanning calorimetry ("DSC") in accordance with ASTM D-3417. Suitable polyolefins may, for instance, include ethylene polymers (e.g., low density polyethylene ("LDPE"), high density polyethylene ("HDPE"), linear low density polyethylene ("LLDPE"), etc.), propylene homopolymers (e.g., syndiotactic, atactic, isotactic, etc.), propylene copolymers, and so forth. In one particular embodiment, the polymer is a propylene polymer, such as homopolypropylene or a copolymer of propylene. The propylene polymer may, for instance, be formed from a substantially isotactic polypropylene homopolymer or a copolymer containing equal to or less than about 10 wt. % of other monomers, i.e., at least about 90% by weight propylene. Such homopolymers may have a melting point of from about 140° C. to about 170° C.

Of course, other polyolefins may also be employed in the composition of the present invention. In one embodiment, for example, the polyolefin may be a copolymer of ethylene or propylene with another α-olefin, such as a $C_3$-$C_{20}$ α-olefin or $C_3$-$C_{12}$ α-olefin. Specific examples of suitable α-olefins include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene or propylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

Exemplary olefin copolymers for use in the present invention include ethylene-based copolymers available under the designation EXACT™ from ExxonMobil Chemical Company of Houston, Tex. Other suitable ethylene copolymers are available under the designation ENGAGE™, AFFINITY™, DOWLEX™ (LLDPE) and ATTANE™ (ULDPE) from Dow Chemical Company of Midland, Mich. Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai, et al.; and U.S. Pat. No. 5,278,272 to Lai, et al. Suitable propylene copolymers are also commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Suitable polypropylene homopolymers may include Exxon Mobil 3155 polypropylene, Exxon Mobil Achieve™ resins, and Total M3661 PP resin. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al.

Any of a variety of known techniques may generally be employed to form the olefin copolymers. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et at, Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl, -1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

B. Nanoinclusion Additive

As used herein, the term "nanoinclusion additive" generally refers to a material that is capable of being dispersed within the polymer matrix in the form of discrete domains of a nano-scale size. For example, prior to drawing, the domains may have an average cross-sectional dimension of from about 1 to about 1000 nanometers, in some embodiments from about 5 to about 800 nanometers, in some embodiments from about 10 to about 500 nanometers, and in some embodiments from about 20 to about 200 nanometers. The domains may have a variety of different shapes, such as elliptical, spherical, cylindrical, plate-like, tubular, etc. In one embodiment, for example, the domains have a substantially elliptical shape. The nanoinclusion additive is typically employed in an amount of from about 0.05 wt. % to about 20 wt. %, in some embodiments from about 0.1 wt. % to about 10 wt. %, and in some embodiments, from about 0.5 wt. % to about 5 wt. % of the thermoplastic composition, based on the weight of the continuous phase polyolefin matrix. The concentration of the nanoinclusion additive in the entire thermoplastic composition may likewise be from about 0.01 wt. % to about 15 wt. %, in some embodiments from about 0.05 wt. % to about 10 wt. %, and in some embodiments, from about 0.3 wt. % to about 6 wt. % of the thermoplastic composition.

The nanoinclusion additive is partially incompatible with the polyolefin in the sense that it can be substantially uniformly distributed within the polyolefin matrix, but in the form of discrete domains. Such partial incompatibility can be accomplished in a variety of ways. In certain embodiments, for example, the nanoinclusion additive may possess a nonpolar component (e.g., olefin) that is compatible with the polyolefin matrix and allows it to become uniformly distributed therein. Nevertheless, the additive may also include a polar component that is incompatible with the polyolefin matrix, thereby allowing it to coalesce or segregate into discrete domains. Such a component may include low or high molecular weight polar molecular segments or blocks, ionic groups, charged or uncharged polar domains, and/or polar molecular groups. Alternatively, the additive may be entirely nonpolar in nature, but possess certain physical properties that still allow for discrete domains to be formed. For example, in certain embodiments, the nanoinclusion additive may be compatible or miscible with the polyolefin above a certain temperature, but phase separate at temperatures lower than the critical solution temperature. In this manner, the nanoinclusion additive can form a stable blend with the polyolefin in the melt phase, but as the temperature decreases, the continuous phase crystallizes and segregates so that the nanoinclusion additive can phase separate, coalesce, and form separate nano-scale domains.

The particular state or form of the nanoinclusion additive is not critical so long as the desired domains can be formed. For example, in some embodiments, the nanoinclusion additive can be in the form of a liquid or semi-solid at room temperature (e.g., 25° C.). Such a liquid can be readily dispersed in the matrix to form a metastable dispersion, and then quenched to preserve the domain size by reducing the temperature of the blend. The kinematic viscosity of such a liquid or semi-solid material is typically from about 0.7 to about 200 centistokes ("cs"), in some embodiments from about 1 to about 100 cs, and in some embodiments, from about 1.5 to about 80 cs, determined at 40° C. Suitable liquids or semi-solids may include, for instance, silicones, silicone-polyether copolymers, aliphatic polyesters, aromatic polyesters, alkylene glycols (e.g., ethylene glycol, diethylene glycol, triethylene glycol, tetraethylene glycol, propylene glycol, polyethylene glycol, polypropylene glycol, polybutylene glycol, etc.), alkane diols (e.g., 1,3-propanediol, 2,2-dimethyl-1,3-propanediol, 1,3-butanediol, 1,4-butanediol, 1,5-pentanediol, 1,6-hexanediol, 2,2,4-trimethyl-1,6 hexanediol, 1,3-cyclohexanedimethanol, 1,4-cyclohexanedimethanol, 2,2,4,4-tetramethyl-1,3-cyclobutanediol, etc.), amine oxides (e.g., octyldimethylamine oxide), fatty acid esters, fatty acid amides (e.g., oleamide, erucamide, stearamide, ethylene bis(stearamide), etc.), mineral, and vegetable oils, and so forth. One particularly suitable liquid or semi-solid is polyether polyol, such as commercially available under the trade name Pluriol® WI from BASF Corp.

In yet other embodiments, the nanoinclusion additive is in the form of a solid, which may be amorphous, crystalline, or semi-crystalline. For example, the nanoinclusion additive may be polymeric in nature and possess a relatively high molecular weight to help improve the melt strength and stability of the thermoplastic composition. As indicated above, the nanoinclusion additive is partially incompatible with the polyolefin matrix. One example of such an additive is a microcrystalline polyolefin wax, which is typically derived from ethylene and/or $C_3$-$C_{10}$-alk-1-enes, such as from propylene, 1-butene, 1-pentene, 1-hexene, 1-heptene, 1-octene, 1-nonene, and 1-decene. Microcrystalline waxes typically have a relatively low melting temperature, such as from about 30° C. to about 150° C., in some embodiments from about 50° C. to about 140° C., and in some embodiments, from about 80° C. to about 130° C. At such low melting temperatures, the wax can form a miscible blend with the polyolefin when in the melt phase, but as the temperature decreases and polymer crystalizes or solidifies, the wax will segregate and coalesce forming separate nanoscale domains.

Another example of a polymeric nanoinclusion additive is a functionalized polyolefin that contains a polar and nonpolar component. The polar component may, for example, be provided by one or more functional groups and the nonpolar component may be provided by an olefin. The olefin component of the nanoinclusion additive may generally be formed from any linear or branched α-olefin monomer, oligomer, or polymer (including copolymers) derived from an olefin monomer, such as described above. The functional group of the nanoinclusion additive may be any group, molecular segment and/or block that provides a polar component to the molecule and is not compatible with the polyolefin matrix polymer. Examples of molecular segment and/or blocks not compatible with polyolefin may include acrylates, styrenics, polyesters, polyamides, etc. The functional group can have an ionic nature and comprise charged metal ions. Particularly suitable functional groups are maleic anhydride, maleic acid, fumaric acid, maleimide, maleic acid hydrazide, a reaction product of maleic anhydride and diamine, methylnadic anhydride, dichloromaleic anhydride, maleic acid amide, etc. Maleic anhydride modified polyolefins are particularly suitable for use in the present invention. Such modified polyolefins are typically formed by grafting maleic anhydride onto a polymeric backbone material. Such maleated polyolefins are available from E. I. du Pont de Nemours and Company under the designation Fusabond®, such as the P Series (chemically modified polypropylene), E Series (chemically modified polyethylene), C Series (chemically modified ethylene vinyl acetate), A Series (chemically modified ethylene acrylate copolymers or terpolymers), or N Series (chemically modified ethylene-propylene, ethylene-propylene diene monomer ("EPDM") or ethylene-octene). Alternatively, maleated polyolefins are also available from Chemtura Corp. under the designation Polybond®, Eastman Chemical Company under the designation Eastman G series, and Arkema under the designation Orevac®.

In certain embodiments, the polymeric nanoinclusion additive may also be reactive. One example of such a reactive nanoinclusion additive is a polyepoxide that contains, on average, at least two oxirane rings per molecule. Without intending to be limited by theory, it is believed that such polyepoxide molecules can undergo a reaction (e.g., chain extension, side chain branching, grafting, copolymer formation, etc.) with certain components of the composition to improve melt strength without significantly reducing glass transition temperature. The reactive additive can also provide compatibilization between the polyolefin and other more polar additives, such as microinclusion additives, and can improve the uniformity of dispersion and reduce the size of microinclusion additives. For example, as will be described in more detail below, certain embodiments of the present invention may employ a polyester as a microinclusion additive. In such embodiments, the reactive nanoinclusion additive may enable a nucleophilic ring-opening reaction via a carboxyl terminal group of the polyester (esterification) or via a hydroxyl group (etherification). Oxazoline side reactions may likewise occur to form ester-amide moieties. Through such reactions, the molecular weight of a polyester microinclusion additive may be increased to counteract the degradation often observed during melt processing. The present inventors have discovered that too much of a reaction can lead to crosslinking between polymer backbones. If such crosslinking is allowed to proceed to a significant extent, the resulting polymer blend can become brittle and difficult to process into a material with the desired strength and elongation properties.

In this regard, the present inventors have discovered that polyepoxides having a relatively low epoxy functionality may be particularly effective, which may be quantified by its "epoxy equivalent weight." The epoxy equivalent weight reflects the amount of resin that contains one molecule of an epoxy group, and it may be calculated by dividing the number average molecular weight of the modifier by the number of epoxy groups in the molecule. The polyepoxide of the present invention typically has a number average molecular weight from about 7,500 to about 250,000 grams per mole, in some embodiments from about 15,000 to about 150,000 grams per mole, and in some embodiments, from about 20,000 to 100,000 grams per mole, with a polydispersity index typically ranging from 2.5 to 7. The polyepoxide may contain less than 50, in some embodiments from 5 to 45, and in some embodiments, from 15 to 40 epoxy groups. In turn, the epoxy equivalent weight may be less than about 15,000 grams per mole, in some embodiments from about 200 to about 10,000 grams per mole, and in some embodiments, from about 500 to about 7,000 grams per mole.

The polyepoxide may be a linear or branched, homopolymer or copolymer (e.g., random, graft, block, etc.) containing terminal epoxy groups, skeletal oxirane units, and/or pendent epoxy groups. The monomers employed to form such polyepoxides may vary. In one particular embodiment, for example, the polyepoxide contains at least one epoxy-functional (meth)acrylic monomeric component. As used herein, the term "(meth)acrylic" includes acrylic and methacrylic monomers, as well as salts or esters thereof, such as acrylate and methacrylate monomers. For example, suitable epoxy-functional (meth)acrylic monomers may include, but are not limited to, those containing 1,2-epoxy groups, such as glycidyl acrylate and glycidyl methacrylate. Other suitable epoxy-functional monomers include allyl glycidyl ether, glycidyl ethacrylate, and glycidyl itoconate.

The polyepoxide typically has a relatively high molecular weight, as indicated above, so that it may not only result in chain extension, but also help to achieve the desired blend morphology. The resulting melt flow rate of the polymer is thus typically within a range of from about 10 to about 200 grams per 10 minutes, in some embodiments from about 40 to about 150 grams per 10 minutes, and in some embodiments, from about 60 to about 120 grams per 10 minutes, determined at a load of 2160 grams and at a temperature of 190° C.

The polyepoxide also typically includes at least one linear or branched α-olefin monomer, such as those having from 2 to 20 carbon atoms and preferably from 2 to 8 carbon atoms. Specific examples include ethylene, propylene, 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are ethylene and propylene. Another suitable monomer may include a (meth)acrylic monomer that is not epoxy-functional. Examples of such (meth)acrylic monomers may include methyl acrylate, ethyl acrylate, n-propyl acrylate, i-propyl acrylate, n-butyl acrylate, s-butyl acrylate, i-butyl acrylate, t-butyl acrylate, n-amyl acrylate, i-amyl acrylate, isobornyl acrylate, n-hexyl acrylate, 2-ethylbutyl acrylate, 2-ethylhexyl acrylate, n-octyl acrylate, n-decyl acrylate, methylcyclohexyl acrylate, cyclopentyl acrylate, cyclohexyl acrylate, methyl methacrylate, ethyl methacrylate, 2-hydroxyethyl methacrylate, n-propyl methacrylate, n-butyl methacrylate, i-propyl methacrylate, i-butyl methacrylate, n-amyl methacrylate, n-hexyl methacrylate, i-amyl methacrylate, s-butyl-methacrylate, t-butyl methacrylate, 2-ethylbutyl methacrylate, methylcyclohexyl methacrylate, cinnamyl methacrylate, crotyl methacrylate, cyclohexyl methacrylate, cyclopentyl methacrylate, 2-ethoxyethyl methacrylate, isobornyl methacrylate, etc., as well as combinations thereof.

In one particularly desirable embodiment of the present invention, the polyepoxide is a terpolymer formed from an epoxy-functional (meth)acrylic monomeric component, α-olefin monomeric component, and non-epoxy functional (meth)acrylic monomeric component. For example, the polyepoxide may be poly(ethylene-co-methylacrylate-co-glycidyl methacrylate), which has the following structure:

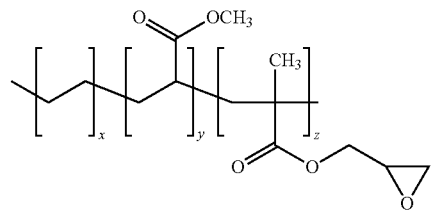

wherein, x, y, and z are 1 or greater.

The epoxy functional monomer may be formed into a polymer using a variety of known techniques. For example, a monomer containing polar functional groups may be grafted onto a polymer backbone to form a graft copolymer. Such grafting techniques are well known in the art and described, for instance, in U.S. Pat. No. 5,179,164. In other embodiments, a monomer containing epoxy functional groups may be copolymerized with a monomer to form a block or random copolymer using known free radical polymerization techniques, such as high pressure reactions, Ziegler-Natta catalyst reaction systems, single site catalyst (e.g., metallocene) reaction systems, etc.

The relative portion of the monomeric component(s) may be selected to achieve a balance between epoxy-reactivity and melt flow rate. More particularly, high epoxy monomer contents can result in good reactivity, but too high of a content may reduce the melt flow rate to such an extent that the polyepoxide adversely impacts the melt strength of the polymer blend. Thus, in most embodiments, the epoxy-functional (meth)acrylic monomer(s) constitute from about 1 wt. % to about 25 wt. %, in some embodiments from about 2 wt. % to about 20 wt. %, and in some embodiments, from about 4 wt. % to about 15 wt. % of the copolymer. The α-olefin monomer(s) may likewise constitute from about 55 wt. % to about 95 wt. %, in some embodiments from about 60 wt. % to about 90 wt. %, and in some embodiments, from about 65 wt. % to about 85 wt. % of the copolymer. When employed, other monomeric components (e.g., non-epoxy functional (meth)acrylic monomers) may constitute from about 5 wt. % to about 35 wt. %, in some embodiments from about 8 wt. % to about 30 wt. %, and in some embodiments, from about 10 wt. % to about 25 wt. % of the copolymer. One specific example of a suitable polyepoxide that may be used in the present invention is commercially available from Arkema under the name LOTADER® AX8950 or AX8900.

LOTADER® AX8950, for instance, has a melt flow rate of 70 to 100 g/10 min and has a glycidyl methacrylate monomer content of 7 wt. % to 11 wt. %, a methyl acrylate monomer content of 13 wt. % to 17 wt. %, and an ethylene monomer content of 72 wt. % to 80 wt. %. Another suitable polyepoxide is commercially available from DuPont under the name ELVALOY® PTW, which is a terpolymer of ethylene, butyl acrylate, and glycidyl methacrylate and has a melt flow rate of 12 g/10 min.

In addition to controlling the type and relative content of the monomers used to form the polyepoxide, the overall weight percentage may also be controlled to achieve the desired benefits. For example, if the modification level is too low, the desired increase in melt strength and mechanical properties may not be achieved. The present inventors have also discovered, however, that if the modification level is too high, processing may be restricted due to strong molecular interactions (e.g., crosslinking) and physical network formation by the epoxy functional groups. Thus, the polyepoxide is typically employed in an amount of from about 0.05 wt. % to about 10 wt. %, in some embodiments from about 0.1 wt. % to about 8 wt. %, in some embodiments from about 0.5 wt. % to about 5 wt. %, and in some embodiments, from about 1 wt. % to about 3 wt. %, based on the weight of the polyolefins employed in the composition. The polyepoxide may also constitute from about 0.05 wt. % to about 10 wt. %, in some embodiments from about 0.05 wt. % to about 8 wt. %, in some embodiments from about 0.1 wt. % to about 5 wt. %, and in some embodiments, from about 0.5 wt. % to about 3 wt. %, based on the total weight of the composition.

Other reactive nanoinclusion additives may also be employed in the present invention, such as oxazoline-functionalized polymers, cyanide-functionalized polymers, etc. When employed, such reactive nanoinclusion additives may be employed within the concentrations noted above for the polyepoxide. In one particular embodiment, an oxazoline-grafted polyolefin may be employed that is a polyolefin grafted with an oxazoline ring-containing monomer. The oxazoline may include a 2-oxazoline, such as 2-vinyl-2-oxazoline (e.g., 2-isopropenyl-2-oxazoline), 2-fatty-alkyl-2-oxazoline (e.g., obtainable from the ethanolamide of oleic acid, linoleic acid, palmitoleic acid, gadoleic acid, erucic acid and/or arachidonic acid) and combinations thereof. In another embodiment, the oxazoline may be selected from ricinoloxazoline maleinate, undecyl-2-oxazoline, soya-2-oxazoline, ricinus-2-oxazoline and combinations thereof, for example. In yet another embodiment, the oxazoline is selected from 2-isopropenyl-2-oxazoline, 2-isopropenyl-4,4-dimethyl-2-oxazoline and combinations thereof.

In certain embodiments of the present invention, multiple nanoinclusion additives may be employed in combination. For instance, a first nanoinclusion additive (e.g., polyepoxide) may be dispersed in the form of domains having an average cross-sectional dimension of from about 50 to about 500 nanometers, in some embodiments from about 60 to about 400 nanometers, and in some embodiments from about 80 to about 300 nanometers. A second nanoinclusion additive may also be dispersed in the form of domains that are smaller than the first nanoinclusive additive, such as those having an average cross-sectional dimension of from about 1 to about 50 nanometers, in some embodiments from about 2 to about 45 nanometers, and in some embodiments from about 5 to about 40 nanometers. When employed, the first and/or second nanoinclusion additives typically constitute from about 0.05 wt. % to about 20 wt. %, in some embodiments from about 0.1 wt. % to about 10 wt. %, and in some embodiments, from about 0.5 wt. % to about 5 wt. % of the thermoplastic composition, based on the weight of the continuous phase (matrix polymer(s)).

The concentration of the first and/or second nanoinclusion additive in the entire thermoplastic composition may likewise be from about 0.01 wt. % to about 15 wt. %, in some embodiments from about 0.05 wt. % to about 10 wt. %, and in some embodiments, from about 0.1 wt. % to about 8 wt. % of the thermoplastic composition.

Nanofillers may optionally be employed for the second nanoinclusion additive, examples of which may include carbon black, carbon nanotubes, carbon nanofibers, nanoclays, metal nanoparticles, nanosilica, nanoalumina, etc. Nanoclays are particularly suitable. The term "nanoclay" generally refers to nanoparticles of a clay material (a naturally occurring mineral, an organically modified mineral, or a synthetic nanomaterial), which typically have a platelet structure. Examples of nanoclays include, for instance, montmorillonite (2:1 layered smectite clay structure), bentonite (aluminium phyllosilicate formed primarily of montmorillonite), kaolinite (1:1 aluminosilicate having a platy structure and empirical formula of $Al_2Si_2O_5(OH)_4$), halloysite (1:1 aluminosilicate having a tubular structure and empirical formula of $Al_2Si_2O_5(OH)_4$), etc. An example of a suitable nanoclay is Cloisite®, which is a montmorillonite nanoclay and commercially available from Southern Clay Products, Inc. Other examples of synthethic nanoclays include but are not limited to a mixed-metal hydroxide nanoclay, layered double hydroxide nanoclay (e.g., sepiocite), laponite, hectorite, saponite, indonite, etc.

If desired, the nanoclay may contain a surface treatment to help improve compatibility with the matrix polymer (e.g., polyester). The surface treatment may be organic or inorganic. In one embodiment, an organic surface treatment is employed that is obtained by reacting an organic cation with the clay. Suitable organic cations may include, for instance, organoquaternary ammonium compounds that are capable of exchanging cations with the clay, such as dimethyl bis[hydrogenated tallow]ammonium chloride (2M2HT), methyl benzyl bis[hydrogenated tallow]ammonium chloride (MB2HT), methyl tris[hydrogenated tallow alkyl] chloride (M3HT), etc. Examples of commercially available organic nanoclays may include, for instance, Dellite® 43B (Laviosa Chimica of Livorno, Italy), which is a montmorillonite clay modified with dimethyl benzylhydrogenated tallow ammonium salt. Other examples include Cloisite® 25A and Cloisite® 30B (Southern Clay Products) and Nanofil 919 (Süd Chemie). If desired, the nanofiller can be blended with a carrier resin to form a masterbatch that enhances the compatibility of the additive with the other polymers in the composition. Particularly suitable carrier resins include, for instance, polyesters (e.g., polylactic acid, polyethylene terephthalate, etc.); polyolefins (e.g., ethylene polymers, propylene polymers, etc.); and so forth, as described in more detail above.

Regardless of the material employed, the nanoinclusion additive is typically selected to have a certain viscosity (or melt flow rate) to ensure that the discrete domains and resulting pores can be adequately maintained. For example, if the viscosity of the nanoinclusion additive is too low (or melt flow rate is too high), it tends to flow and disperse uncontrollably through the continuous phase. This results in lamellar, plate-like domains or co-continuous phase structures that are difficult to maintain and also likely to prematurely fracture. Conversely, if the viscosity is too high (or melt flow rate is too low), it tends to clump together and form very large elliptical domains, which are difficult to disperse during blending. This may cause uneven distribution of the nanoinclusion additive through the entirety of the continuous phase. For instance, the ratio of the melt flow rate of the polyolefin to the melt flow rate of a polymeric nanoinclusion additive, for instance, may be from about 0.2 to about 8, in some embodiments from about 0.5 to about 6, and in some embodiments, from about 1 to about 5. The nanoinclusion additive may, for example, have a melt flow rate (on a dry basis) of from about 0.1 to about 100 grams per 10 minutes, in some embodiments from about 0.5 to about 50 grams per 10 minutes, and in some embodiments, from about 5 to about 15 grams per 10 minutes, determined at a load of 2160 grams and at a temperature at least about 40° C. above the melting temperature (e.g., at 190° C.) in accordance with ASTM D1238. The polyolefin may likewise have a melt flow rate (on a dry basis) of from about 0.5 to about 80 grams per 10 minutes, in some embodiments from about 1 to about 40 grams per 10 minutes, and in some embodiments, from about 5 to about 20 grams per 10 minutes, determined at a load of 2160 grams and at a temperature at least about 40° C. above the melting temperature (e.g., at 230° C.) in accordance with ASTM D1238.

C. Microinclusion Additive

Although not required, the composition of the present invention may also employ a microinclusion additive. As used herein, the term "microinclusion additive" generally refers to any material that is capable of being dispersed within the polymer matrix in the form of discrete domains of a micro-scale size. For example, prior to drawing, the domains may have an average cross-sectional dimension of from about 0.1 µm to about 25 µm, in some embodiments from about 0.5 µm to about 20 µm, and in some embodiments from about 1 µm to about 10 µm. When employed, the present inventors have discovered that the micro-scale and nano-scale phase domains are able to interact in a unique manner when subjected to a deformation and elongational strain (e.g., drawing) to create a network of pores. Namely, it is believed that elongational strain can initiate intensive localized shear zones and/or stress intensity zones (e.g., normal stresses) near the micro-scale discrete phase domains as a result of stress concentrations that arise from the incompatibility of the materials. These shear and/or stress intensity zones cause some initial debonding in the polyolefin matrix adjacent to the micro-scale domains. Notably, however, the localized shear and/or stress intensity zones created near the nano-scale discrete phase domains may overlap with the micro-scale zones to cause even further debonding to occur in the polymer matrix, thereby creating a substantial number of nanopores adjacent to the nano-scale domains and/or micro-scale domains.

The particular nature of the microinclusion additive is not critical, and may include liquids, semi-solids, or solids (e.g., amorphous, crystalline, or semi-crystalline). In certain embodiments, the microinclusion additive is polymeric in nature and possesses a relatively high molecular weight to help improve the melt strength and stability of the thermoplastic composition. Typically, the microinclusion additive polymer may be generally incompatible with the matrix polymer. In this manner, the additive can better become dispersed as discrete phase domains within a continuous phase of the matrix polymer. The discrete domains are capable of absorbing energy that arises from an external force, which increases the overall toughness and strength of the resulting material. The domains may have a variety of different shapes, such as elliptical, spherical, cylindrical, plate-like, tubular, etc. In one embodiment, for example, the domains have a substantially elliptical shape. The physical dimension of an individual domain is typically small enough to minimize the propagation of cracks through the polymeric material upon the application of an external stress, but large enough to initiate microscopic plastic deformation and allow for shear zones at and around particle inclusions.

The microinclusion additive may have a certain melt flow rate (or viscosity) to ensure that the discrete domains and resulting pores can be adequately maintained. For example, if the melt flow rate of the additive is too high, it tends to flow and disperse uncontrollably through the continuous phase. This results in lamellar, plate-like domains or co-continuous phase structures that are difficult to maintain and also likely to prematurely fracture. Conversely, if the melt flow rate of the additive is too low, it tends to clump together and form very large elliptical domains, which are difficult to disperse during blending. This may cause uneven distribution of the additive through the entirety of the continuous phase. In this regard, the present inventors have discovered that the ratio of the melt flow rate of the microinclusion additive to the melt flow rate of the matrix polymer is typically from about 0.5 to about 10, in some embodiments from about 1 to about 8, and in some embodiments, from about 2 to about 6. The microinclusion additive may, for example, have a melt flow rate of from about 5 to about 200 grams per 10 minutes, in some embodiments from about 20 to about 150 grams per 10 minutes, and in some embodiments, from about 40 to about 100 grams per 10 minutes, determined at a load of 2160 grams and at a temperature at least about 40° C. above its melting temperature (e.g., 210° C.).

In addition to the properties noted above, the mechanical characteristics of the microinclusion additive may also be selected to achieve the desired porous network. For example, applied with an external force, stress concentrations (e.g., including normal or shear stresses) and shear and/or plastic yielding zones may be initiated at and around the discrete phase domains as a result of stress concentrations that arise from a difference in the elastic modulus of the additive and matrix polymer. Larger stress concentrations promote more intensive localized plastic flow at the domains, which allows them to become significantly elongated when stresses are imparted. These elongated domains can allow the composition to exhibit a more pliable and softer behavior. To enhance the stress concentrations, the microinclusion additive may be selected to have a relatively high Young's modulus of elasticity in comparison to the polyolefin matrix. For example, the ratio of the modulus of elasticity of the additive to that of polyolefin matrix is typically from about 1 to about 250, in some embodiments from about 2 to about 100, and in some embodiments, from about 2 to about 50. The modulus of elasticity of the microinclusion additive may, for instance, range from about 200 to about 3,500 Megapascals (MPa), in some embodiments from about 300 to about 2,000 MPa, and in some embodiments, from about 400 to about 1,500 MPa. To the contrary, the modulus of elasticity of the polyolefin may, for instance, range from about 100 to about 1,500 MPa, and in some embodiments, from about 200 to about 1000 MPa. Alternatively, the modulus of elasticity of microinclusion additive can be lower than the modulus of elasticity of polyolefin matrix. The modulus of elasticity may, for example, range from about 10 MPa to about 100 MPa, and optionally from about 20 MPA to about 80 MPa.

While a wide variety of microinclusion additives may be employed that have the properties identified above, particularly suitable examples of such additives may include styrenic copolymers (e.g., styrene-butadiene-styrene, styrene-isoprene-styrene, styrene-ethylene-propylene-styrene, styrene-ethylene-butadiene-styrene, etc.); fluoropolymers, such as polyvinyl chloride (PVC), polytetrafluoroethylene (PTFE), polychlorotrifluoroethylene (PCTFE), etc.; polyvinyl alcohols; polyvinyl acetates; polyesters, such as aliphatic polyesters, such as polycaprolactone, polyesteramides, polylactic acid (PLA) and its copolymers, polyglycolic acid, polyalkylene carbonates (e.g., polyethylene carbonate), poly-3-hydroxybutyrate (PHB), poly-3-hydroxyvalerate (PHV), poly-3-hydroxybutyrate-co-4-hydroybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.), aliphatic-aromatic copolyesters (e.g., polybutylene adipate terephthalate, polyethylene adipate terephthalate, polyethylene adipate isophthalate, polybutylene adipate isophthalate, etc.), aromatic polyesters (e.g., polyethylene terephthalate, polybutylene terephthalate, etc.); and so forth.

Particularly suitable are microinclusion additives that are generally rigid in nature to the extent that they have a relatively high glass transition temperature. For example, the glass transition temperature ("$T_g$") may be about 0° C. or more, in some embodiments from about 5° C. to about 100° C., in some embodiments from about 30° C. to about 80° C., and in some embodiments, from about 50° C. to about 75° C. The glass transition temperature may be determined by dynamic mechanical analysis in accordance with ASTM E1640-09.

One particularly suitable rigid polyester is polylactic acid, which may generally be derived from monomer units of any isomer of lactic acid, such as levorotory-lactic acid ("L-lactic acid"), dextrorotatory-lactic acid ("D-lactic acid"), meso-lactic acid, or mixtures thereof. Monomer units may also be formed from anhydrides of any isomer of lactic acid, including L-lactide, D-lactide, meso-lactide, or mixtures thereof. Cyclic dimers of such lactic acids and/or lactides may also be employed. Any known polymerization method, such as polycondensation or ring-opening polymerization, may be used to polymerize lactic acid. A small amount of a chain-extending agent (e.g., a diisocyanate compound, an epoxy compound or an acid anhydride) may also be employed. The polylactic acid may be a homopolymer or a copolymer, such as one that contains monomer units derived from L-lactic acid and monomer units derived from D-lactic acid. Although not required, the rate of content of one of the monomer unit derived from L-lactic acid and the monomer unit derived from D-lactic acid is preferably about 85 mole % or more, in some embodiments about 90 mole % or more, and in some embodiments, about 95 mole % or more. Multiple polylactic acids, each having a different ratio between the monomer unit derived from L-lactic acid and the monomer unit derived from D-lactic acid, may be blended at an arbitrary percentage. Of course, polylactic acid may also be blended with other types of polymers (e.g., polyolefins, polyesters, etc.).

In one particular embodiment, the polylactic acid has the following general structure:

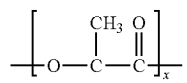

One specific example of a suitable polylactic acid polymer that may be used in the present invention is commercially available from Biomer, Inc. of Krailling, Germany) under the name BIOMER™ L9000. Other suitable polylactic acid polymers are commercially available from Natureworks LLC of Minnetonka, Minn. (NATUREWORKS®) or Mitsui Chemical (LACEA™). Still other suitable polylactic acids may be described in U.S. Pat. Nos. 4,797,468; 5,470,944; 5,770,682; 5,821,327; 5,880,254; and 6,326,458, which are incorporated herein in their entirety by reference thereto for all purposes.

The polylactic acid typically has a number average molecular weight ("$M_n$") ranging from about 40,000 to about 180,000 grams per mole, in some embodiments from about 50,000 to about 160,000 grams per mole, and in some embodiments, from about 80,000 to about 120,000 grams per mole. Likewise, the polymer also typically has a weight average molecular weight ("$M_w$") ranging from about 80,000 to about 250,000 grams per mole, in some embodiments from about 100,000 to about 200,000 grams per mole, and in some embodiments, from about 110,000 to about 160,000 grams per mole. The ratio of the weight average molecular weight to the number average molecular weight ("$M_w/M_n$"), i.e., the "polydispersity index", is also relatively low. For example, the polydispersity index typically ranges from about 1.0 to about 3.0, in some embodiments from about 1.1 to about 2.0, and in some embodiments, from about 1.2 to about 1.8. The weight and number average molecular weights may be determined by methods known to those skilled in the art.

Some types of neat polyesters (e.g., polylactic acid) can absorb water from the ambient environment such that it has a moisture content of about 500 to 600 parts per million ("ppm"), or even greater, based on the dry weight of the starting polylactic acid. Moisture content may be determined in a variety of ways as is known in the art, such as in accordance with ASTM D 7191-05, such as described below. Because the presence of water during melt processing can hydrolytically degrade the polyester and reduce its molecular weight, it is sometimes desired to dry the polyester prior to blending. In most embodiments, for example, it is desired that the renewable polyester have a moisture content of about 300 parts per million ("ppm") or less, in some embodiments about 200 ppm or less, in some embodiments from about 1 to about 100 ppm prior to blending with the microinclusion additive. Drying of the polyester may occur, for instance, at a temperature of from about 50° C. to about 100° C., and in some embodiments, from about 70° C. to about 80° C.

Regardless of the materials employed, the relative percentage of the microinclusion additive in the thermoplastic composition is selected to achieve the desired properties without significantly impacting the resulting composition. For example, the microinclusion additive is typically employed in an amount of from about 1 wt. % to about 30 wt. %, in some embodiments from about 2 wt. % to about 25 wt. %, and in some embodiments, from about 5 wt. % to about 20 wt. % of the thermoplastic composition, based on the weight of the polyolefin matrix employed in the composition. The concentration of the microinclusion additive in the entire thermoplastic composition may likewise constitute from about 0.1 wt. % to about 30 wt. %, in some embodiments from about 0.5 wt. % to about 25 wt. %, and in some embodiments, from about 1 wt. % to about 20 wt. %.

D. Other Components

A wide variety of ingredients may be employed in the composition for a variety of different reasons. For instance, in one particular embodiment, an interphase modifier may be employed in the thermoplastic composition to help reduce the degree of friction and connectivity between the nanoinclusion and/or microinclusion additives and polyolefin matrix, and thus enhance the degree and uniformity of debonding. In this manner, the pores can become distributed in a more homogeneous fashion throughout the composition. The modifier may be in a liquid or semi-solid form at room temperature (e.g., 25° C.) so that it possesses a relatively low viscosity, allowing it to be more readily incorporated into the thermoplastic composition and to easily migrate to the polymer surfaces. By reducing physical forces at the interfaces of the polyolefin matrix and the additive, it is believed that the low viscosity, hydrophobic nature of the modifier can help facilitate debonding. As used herein, the term "hydrophobic" typically refers to a material having a contact angle of water in air of about 40° or more, and in some cases, about 60° or more. In contrast, the term "hydrophilic" typically refers to a material having a contact angle of water in air of less than about 40°. One suitable test for measuring the contact angle is ASTM D5725-99 (2008).

Although not required, the interphase modifier may be particularly suitable in embodiments in which a microinclusion additive is employed and in which the nanoinclusion additive is a solid (e.g., polymeric material). Suitable hydrophobic, low viscosity interphase modifiers may include, for instance, the liquids and/or semi-solids referenced above. One particularly suitable interphase modifier is polyether polyol, such as commercially available under the trade name PLURIOL® WI from BASF Corp. Another suitable modifier is a partially renewable ester, such as commercially available under the trade name HALLGREEN® IM from Hallstar.

When employed, the interphase modifier may constitute from about 0.1 wt. % to about 20 wt. %, in some embodiments from about 0.5 wt. % to about 15 wt. %, and in some embodiments, from about 1 wt. % to about 10 wt. % of the thermoplastic composition, based on the weight of the continuous phase polyolefin matrix. The concentration of the interphase modifier in the entire thermoplastic composition may likewise constitute from about 0.05 wt. % to about 20 wt. %, in some embodiments from about 0.1 wt. % to about 15 wt. %, and in some embodiments, from about 0.5 wt. % to about 10 wt. %. In the amounts noted above, the interphase modifier has a character that enables it to readily migrate to the interfacial surface of the polymers and facilitate debonding without disrupting the overall melt properties of the thermoplastic composition. For example, the melt flow rate of the thermoplastic composition may also be similar to that of the polyolefin matrix. For example, the melt flow rate of the composition (on a dry basis) may be from about 0.1 to about 250 grams per 10 minutes, in some embodiments from about 0.5 to about 200 grams per 10 minutes, and in some embodiments, from about 5 to about 150 grams per 10 minutes, determined at a load of 2160 grams and at 190° C. in accordance with ASTM D1238.

Compatibilizers may also be employed that improve interfacial adhesion and reduce the interfacial tension between the domain and the matrix, thus allowing the formation of smaller domains during mixing. Examples of suitable compatibilizers may include, for instance, copolymers functionalized with epoxy or maleic anhydride chemical moieties. An example of a maleic anhydride compatibilizer is polypropylene-grafted-maleic anhydride, which is commercially available from Arkema under the trade names Orevac™ 18750 and Orevac™ CA 100. When employed, compatibilizers may constitute from about 0.05 wt. % to about 10 wt. %, in some embodiments from about 0.1 wt. % to about 8 wt. %, and in some embodiments, from about 0.5 wt. % to about 5 wt. % of the thermoplastic composition, based on the weight of the continuous phase polyolefin matrix.

Other suitable materials that may also be used in the thermoplastic composition, such as catalysts, antioxidants, stabilizers, surfactants, waxes, solid solvents, nucleating agents, particulates, nanofillers, and other materials added to enhance the processability and mechanical properties of the thermoplastic composition. Nevertheless, one beneficial aspect of the present invention is that good properties may be provided without the need for various conventional additives, such as blowing agents (e.g., chlorofluorocarbons, hydrochlorofluorocarbons, hydrocarbons, carbon dioxide, supercritical carbon dioxide, nitrogen, etc.) and pore-initiating inorganic oxide fillers (e.g., calcium carbonate). In fact, the thermoplastic composition may be generally free of blowing agents and/or pore-initiating inorganic oxide fillers. For example, such blowing agents and/or fillers may be present in an amount of no more than about 1 wt. %, in some embodiments no more than about 0.5 wt. %, and in some embodiments, from about 0.001 wt. % to about 0.2 wt. % of the thermoplastic composition. Further, due to its stress whitening properties, as described in more detail below, the resulting composition may achieve an opaque color (e.g., white) without the need for conventional pigments, such as titanium dioxide. In certain embodiments, for example, pigments may be present in an amount of no more than about 1 wt. %, in some embodiments no more than about 0.5 wt. %, and in some embodiments, from about 0.001 wt. % to about 0.2 wt. % of the thermoplastic composition.

II. Polyolefin Material

The polyolefin material of the present invention may generally formed by drawing the thermoplastic composition. To form the initial thermoplastic composition, the components are typically blended together using any of a variety of known techniques. In one embodiment, for example, the components may be supplied separately or in combination. For instance, the components may first be dry mixed together to form an essentially homogeneous dry mixture, and they may likewise be supplied either simultaneously or in sequence to a melt processing device that dispersively blends the materials. Batch and/or continuous melt processing techniques may be employed. For example, a mixer/kneader, Banbury mixer, Farrel continuous mixer, single-screw extruder, twin-screw extruder, roll mill, etc., may be utilized to blend and melt process the materials. Particularly suitable melt processing devices may be a co-rotating, twin-screw extruder (e.g., ZSK-30 extruder available from Werner & Pfleiderer Corporation of Ramsey, N.J. or a Thermo Prism™ USALAB 16 extruder available from Thermo Electron Corp., Stone, England). Such extruders may include feeding and venting ports and provide high intensity distributive and dispersive mixing. For example, the components may be fed to the same or different feeding ports of the twin-screw extruder and melt blended to form a substantially homogeneous melted mixture. If desired, other additives may also be injected into the polymer melt and/or separately fed into the extruder at a different point along its length.

Regardless of the particular processing technique chosen, the resulting melt blended composition typically contains nano-scale domains of the nanoinclusion additive and optionally micro-scale domains of the microinclusion additive. The degree of shear/pressure and heat may be controlled to ensure sufficient dispersion, but not so high as to adversely reduce the size of the domains so that they are incapable of achieving the desired properties. For example, blending typically occurs at a temperature of from about 180° C. to about 300° C., in some embodiments from about 185° C. to about 250° C., and in some embodiments, from about 190° C. to about 240° C. Likewise, the apparent shear rate during melt processing may range from about 10 seconds$^{-1}$ to about 3000 seconds$^{-1}$, in some embodiments from about 50 seconds$^{-1}$ to about 2000 seconds$^{-1}$, and in some embodiments, from about 100 seconds$^{-1}$ to about 1200 seconds$^{-1}$. The apparent shear rate may be equal to $4Q/\pi R^3$, where Q is the volumetric flow rate ("m$^3$/s") of the polymer melt and R is the radius ("m") of the capillary (e.g., extruder die) through which the melted polymer flows. Of course, other variables, such as the residence time during melt processing, which is inversely proportional to throughput rate, may also be controlled to achieve the desired degree of homogeneity.

To achieve the desired shear conditions (e.g., rate, residence time, shear rate, melt processing temperature, etc.), the speed of the extruder screw(s) may be selected within a certain range. Generally, an increase in product temperature is observed with increasing screw speed due to the additional mechanical energy input into the system. For example, the screw speed may range from about 50 to about 600 revolutions per minute ("rpm"), in some embodiments from about 70 to about 500 rpm, and in some embodiments, from about 100 to about 300 rpm. This may result in a temperature that is sufficiently high to disperse the nanoinclusion additive without adversely impacting the size of the resulting domains. The melt shear rate, and in turn the degree to which the additives are dispersed, may also be increased through the use of one or more distributive and/or dispersive mixing elements within the mixing section of the extruder. Suitable distributive mixers for single screw extruders may include, for instance, Saxon, Dulmage, Cavity Transfer mixers, etc. Likewise, suitable dispersive mixers may include Blister ring, Leroy/Maddock, CRD mixers, etc. As is well known in the art, the mixing may be further improved by using pins in the barrel that create a folding and reorientation of the polymer melt, such as those used in Buss Kneader extruders, Cavity Transfer mixers, and Vortex Intermeshing Pin (VIP) mixers.

Regardless of the particular manner in which it is formed, the composition may be drawn in the longitudinal direction (e.g., machine direction), transverse direction (e.g., cross-machine direction), etc., as well as combinations thereof, to form a porous network. If desired, the composition may be drawn in-line as it is being formed in to a film, fiber, etc. Alternatively, the composition may be drawn in its solid state after being formed into a film, fiber, etc., before and/or after lamination to any optional materials. By "solid state" drawing, it is generally meant that the composition is kept at a temperature below the melting temperature of the polyolefin matrix polymer. Among other things, this helps to ensure that the polymer chains are not altered to such an extent that the porous network becomes unstable. For example, the composition may be drawn at a temperature of from about −50° C. to about 150° C., in some embodiments from about −40° C. to about 140° C., in some embodiments, from about −20° C. to about 100° C., and in some embodiments, from about 0° C. to about 50° C. In certain cases, the drawing temperature may optionally be at least about 10° C., in some embodiments at least about 20° C., and in some embodiments, at least about 30° C. below the glass transition temperature of the component having the highest glass transition temperature (e.g., microinclusion additive). In such embodiments, the composition may be drawn at a temperature of from about 0° C. to about 50° C., in some embodiments from about 15° C. to about 40° C., and in some embodiments, from about 20° C. to about 30° C.

To perform the desired drawing, the thermoplastic composition may be formed into a precursor shape, drawn, and thereafter converted into the desired material (e.g., film, fiber, molded article, etc.). In one embodiment, the precursor shape may be a film having a thickness of from about 1 to about 5000 micrometers, in some embodiments from about 2 to about 4000 micrometers, in some embodiments from about 5 to about 2500 micrometers, and in some embodiments, from about 10 to about 500 micrometers. As an alternative to forming a precursor shape, the thermoplastic composition may also be drawn in situ as it is being shaped into the desired form for the polyolefin material. In one embodiment, for example, the thermoplastic composition may be drawn as it is being formed into a film or fiber.

Regardless, various drawing techniques may be employed, such as aspiration (e.g., fiber draw units), tensile frame drawing, biaxial drawing, multi-axial drawing, profile drawing, vacuum drawing, etc. In one embodiment, for example, the composition is drawn with a machine direction orienter ("MDO"), such as commercially available from Marshall and Willams, Co. of Providence, R.I. MDO units typically have a plurality of drawing rolls (e.g., from 5 to 8) which progressively draw and thin the film in the machine direction. The composition may be drawn in either single or multiple discrete drawing operations. It should be noted that some of the rolls in an MDO apparatus may not be operating at progressively higher speeds. To draw the composition in the manner described above, it is typically desired that the rolls of the MDO are not heated. Nevertheless, if desired, one or more rolls may be heated to a slight extent to facilitate the drawing process so long as the temperature of the composition remains below the ranges noted above.

The degree of drawing depends in part of the nature of the material being drawn (e.g., fiber, film, etc.). The composition is typically drawn (e.g., in the machine direction) to a draw ratio of from about 1.1 to about 3.5, in some embodiments from about 1.2 to about 3.0, and in some embodiments, from about 1.3 to about 2.5. The draw ratio may be determined by dividing the length of the drawn material by its length before drawing. The draw rate may also vary to help achieve the desired properties, such as within the range of from about 5% to about 1500% per minute of deformation, in some embodiments from about 20% to about 1000% per minute of deformation, and in some embodiments, from about 25% to about 850% per minute of deformation. Although the composition is typically drawn without the application of external heat (e.g., heated rolls), such heat might be optionally employed to improve processability, reduce draw force, increase draw rates, and improve fiber uniformity.

Drawing in the manner described above can result in the formation of pores that have a "nano-scale" cross-sectional dimension ("nanopores"), such as about 800 nanometers or less, in some embodiments from about 5 to about 700 nanometers, and in some embodiments, from about 10 to about 500 nanometers. The nanopores may also have an average axial dimension (e.g., length) of from about 100 to about 5000 nanometers, in some embodiments from about 50 to about 2000 nanometers, and in some embodiments, from about 100 to about 1000 nanometers. Micropores may also be formed during drawing that have an average cross-sectional dimension of about 0.2 micrometers or more, in some embodiments about 0.5 micrometers or more, and in some embodiments, from about 0.5 micrometers to about 5 micrometers. In certain cases, the axial dimension of the micropores and/or nanopores may be larger than the cross-sectional dimension so that the aspect ratio (the ratio of the axial dimension to the cross-sectional dimension) is from about 1 to about 30, in some embodiments from about 1.1 to about 15, and in some embodiments, from about 1.2 to about 5. For example, the axial dimension of the micropores may be 1 micrometer or more, in some embodiments about 1.5 micrometers or more, and in some embodiments, from about 2 to about 30 micrometers.

Regardless of their particular size, the present inventors have discovered that the pores (e.g., nanopores, micropores, or both) can be distributed in a substantially homogeneous fashion throughout the material. For example, the pores may be distributed in columns that are oriented in a direction generally perpendicular to the direction in which a stress is applied. These columns may be generally parallel to each other across the width of the material. Without intending to be limited by theory, it is believed that the presence of such a homogeneously distributed porous network can result in a high thermal resistance as well as good mechanical properties (e.g., energy dissipation under load and impact strength). This is in stark contrast to conventional techniques for creating pores that involve the use of blowing agents, which tend to result in an uncontrolled pore distribution and poor mechanical properties.

In addition to forming a porous network, drawing can also significantly increase the axial dimension of certain of the discrete domains so that they have a generally linear, elongated shape. For example, the elongated micro-scale domains may have an average axial dimension that is about 10% or more, in some embodiments from about 20% to about 500%, and in some embodiments, from about 50% to about 250% greater than the axial dimension of the domains prior to drawing. The axial dimension (e.g., length) after drawing may, for instance, range from about 1 µm to about 400 µm, in some embodiments from about 5 µm to about 200 µm, and in some embodiments from about 10 µm to about 150 µm. The micro-scale domains may also be relatively thin and thus have a small cross-sectional dimension, such as from about 0.02 to about 20 micrometers, in some embodiments from about 0.1 to about 10 micrometers, and in some embodiments, from 0.4 to about 5 micrometers. This may result in an aspect ratio for the domains (the ratio of the axial dimension to a dimension orthogonal to the axial dimension) of from about 2 to about 150, in some embodiments from about 3 to about 100, and in some embodiments, from about 4 to about 50. Due to their small size, the nano-scale domains are not typically elongated in the same manner as the micro-scale domains. Thus, the nano-scale domains may retain an average axial dimension (e.g., length) of from about 1 to about 1000 nanometers, in some embodiments from about 5 to about 800 nanometers, in some embodiments from about 10 to about 500 nanometers, and in some embodiments from about 20 to about 200 nanometers.

III. Articles

Due to its unique and beneficial properties, the resulting polyolefin material of the present invention is well suited for use in a variety of different types of articles, such as an absorbent article, packaging film, barrier film, medical product (e.g., gown, surgical drape, facemask, head covering, surgical cap, shoe covering, sterilization wrap, warming blanket, heating pad, etc.), and so forth. For example, the polyolefin material may be incorporated into an "absorbent article" that is capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, mitt wipe, and so forth; medical absorbent articles, such as garments, fenestration materials, underpads, bedpads, bandages, absorbent drapes, and medical wipes; food service wipers; clothing articles; pouches, and so forth. Materials and processes suitable for forming such articles are well known to those skilled in the art. Absorbent articles, for instance, typically include a substantially liquid-impermeable layer (e.g., outer cover), a liquid-permeable layer (e.g., bodyside liner, surge layer, etc.), and an absorbent core. In one embodiment, for example, the polyolefin material may be in the form of a fibrous material (e.g., nonwoven web) and used to form an outer cover of an absorbent article. If desired, the nonwoven web may be laminated to a liquid-impermeable film that is either vapor-permeable or vapor-impermeable. The polyolefin material may likewise be in the form of a film that is used in an absorbent article, such as a liquid-impermeable film of the outer cover, which is either vapor-permeable or vapor-impermeable.

In this regard, one particular embodiment of an absorbent article that may employ the polyolefin material of the present invention will now be described in more detail. For instance, the absorbent article may include a main body portion containing a topsheet, an outer cover or backsheet, an absorbent core positioned between the backsheet and the topsheet, and a pair of flaps extending from each longitudinal side of the main body portion. The topsheet defines a bodyfacing surface of the absorbent article. The absorbent core is positioned inward from the outer periphery of the absorbent article and includes a body-facing side positioned adjacent the topsheet and a garment-facing surface positioned adjacent the backsheet. In one particular embodiment of the present invention, the backsheet is a film formed from the polyolefin material of the present invention and is generally liquid-impermeable and optionally vapor-permeable. The film used to form the backsheet may also be laminated to one or more nonwoven web facings such as described above.

The topsheet is generally designed to contact the body of the user and is liquid-permeable. The topsheet may surround the absorbent core so that it completely encases the absorbent article. Alternatively, the topsheet and the backsheet may extend beyond the absorbent core and be peripherally joined together, either entirely or partially, using known techniques. Typically, the topsheet and the backsheet are joined by adhesive bonding, ultrasonic bonding, or any other suitable joining method known in the art. The topsheet is sanitary, clean in appearance, and somewhat opaque to hide bodily discharges collected in and absorbed by the absorbent core. The topsheet further exhibits good strike-through and rewet characteristics permitting bodily discharges to rapidly penetrate through the topsheet to the absorbent core, but not allow the body fluid to flow back through the topsheet to the skin of the wearer. For example, some suitable materials that may be used for the topsheet include nonwoven materials, perforated thermoplastic films, or combinations thereof. A nonwoven fabric made from polyester, polyethylene, polypropylene, bicomponent, nylon, rayon, or like fibers may be utilized. For instance, a white uniform spunbond material is particularly desirable because the color exhibits good masking properties to hide menses that has passed through it. U.S.

Pat. No. 4,801,494 to Datta, et al. and U.S. Pat. No. 4,908,026 to Sukiennik. et al. teach various other cover materials that may be used in the present invention.

The topsheet may also contain a plurality of apertures formed therethrough to permit body fluid to pass more readily into the absorbent core. The apertures may be randomly or uniformly arranged throughout the topsheet, or they may be located only in the narrow longitudinal band or strip arranged along the longitudinal axis of the absorbent article. The apertures permit rapid penetration of body fluid down into the absorbent core. The size, shape, diameter and number of apertures may be varied to suit one's particular needs.

The absorbent article may also contain an absorbent core positioned between the topsheet and the backsheet. The absorbent core may be formed from a single absorbent member or a composite containing separate and distinct absorbent members. It should be understood, however, that any number of absorbent members may be utilized in the present invention. For example, in an embodiment, the absorbent core may contain an intake member positioned between the topsheet and a transfer delay member. The intake member may be made of a material that is capable of rapidly transferring, in the z-direction, body fluid that Is delivered to the topsheet. The intake member may generally have any shape and/or size desired. In one embodiment, the intake member has a rectangular shape, with a length equal to or less than the overall length of the absorbent article, and a width less than the width of the absorbent article. For example, a length of between about 150 mm to about 300 mm and a width of between about 10 mm to about 60 mm may be utilized.

Any of a variety of different materials may be used for the intake member to accomplish the above-mentioned functions. The material may be synthetic, cellulosic, or a combination of synthetic and cellulosic materials. For example, airlaid cellulosic tissues may be suitable for use in the intake member. The airlaid cellulosic tissue may have a basis weight ranging from about 10 grams per square meter (gsm) to about 300 gsm, and in some embodiments, between about 100 gsm to about 250 gsm. In one embodiment, the airlaid cellulosic tissue has a basis weight of about 200 gsm. The airlaid tissue may be formed from hardwood and/or softwood fibers. The airlaid tissue has a fine pore structure and provides an excellent wicking capacity, especially for menses.

If desired, a transfer delay member may be positioned vertically below the intake member. The transfer delay member may contain a material that is less hydrophilic than the other absorbent members, and may generally be characterized as being substantially hydrophobic. For example, the transfer delay member may be a nonwoven fibrous web composed of a relatively hydrophobic material, such as polypropylene, polyethylene, polyester or the like, and also may be composed of a blend of such materials. One example of a material suitable for the transfer delay member is a spunbond web composed of polypropylene, multi-lobal fibers. Further examples of suitable transfer delay member materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay member are described in U.S. Pat. No. 4,798,603 to Meyer, et al. and U.S. Pat. No. 5,248,309 to Serbiak, et al. To adjust the performance of the invention, the transfer delay member may also be treated with a selected amount of surfactant to increase its initial wettability.

The transfer delay member may generally have any size, such as a length of about 150 mm to about 300 mm. Typically, the length of the transfer delay member is approximately equal to the length of the absorbent article. The transfer delay member may also be equal in width to the intake member, but is typically wider. For example, the width of the transfer delay member may be from between about 50 mm to about 75 mm, and particularly about 48 mm. The transfer delay member typically has a basis weight less than that of the other absorbent members. For example, the basis weight of the transfer delay member is typically less than about 150 grams per square meter (gsm), and in some embodiments, between about 10 gsm to about 100 gsm. In one particular embodiment, the transfer delay member is formed from a spunbonded web having a basis weight of about 30 gsm.

Besides the above-mentioned members, the absorbent core may also include a composite absorbent member, such as a coform material. In this instance, fluids may be wicked from the transfer delay member into the composite absorbent member. The composite absorbent member may be formed separately from the intake member and/or transfer delay member, or may be formed simultaneously therewith. In one embodiment, for example, the composite absorbent member may be formed on the transfer delay member or intake member, which acts a carrier during the coform process described above.

The polyolefin material may also be employed in a wide variety of other types of articles. Non-limiting examples include, for instance, insulation materials for refrigeration units (e.g., refrigerators, freezers, vending machines, etc.); automotive components (e.g., front and rear seats, headrests, armrests, door panels, rear shelves/package trays, steering wheels and interior trim, dashboards, etc.); building panels and sections (e.g., roofs, wall cavities, under floors, etc.); apparel (e.g., coats, shirts, pants, gloves, aprons, coveralls, shoes, boots, headware, sock liners, etc.); furniture and bedding (e.g., sleeping bags, comforters, etc.); fluid storage/transfer systems (e.g., pipes or tankers for liquid/gas hydrocarbons, liquid nitrogen, oxygen, hydrogen, or crude oil); extreme environments (e.g., underwater or space); food and beverage products (e.g., cups, cup holders, plates, etc.); containers and bottles; and so forth. The polyolefin material may also be used in a "garment", which is generally meant to include any article that is shaped to fit over a portion of a body. Examples of such articles include, without limitation, clothing (e.g., shirts, pants, jeans, slacks, skirts, coats, activewear, athletic, aerobic, and exercise apparel, swimwear, cycling jerseys or shorts, swimsuit/bathing suit, race suit, wetsuit, bodysuit, etc.), footwear (e.g., shoes, socks, boots, etc.), protective apparel (e.g., firefighter's coat), clothing accessories (e.g., belts, bra straps, side panels, gloves, hosiery, leggings, orthopedic braces, etc.), undergarments (e.g., underwear, t-shirts, etc.), compression garments, draped garments (e.g., kilts loincloths, togas, ponchos, cloaks, shawls, etc.), and so forth.

The polyolefin material may be employed in a wide variety of articles within any particular application. For example, when considering automotive applications, the polyolefin material may be employed in fibrous articles or as solid moldings. By way of example, fibers of the polyolefin material may be beneficially employed in articles that can enhance comfort and/or aesthetics of a vehicle (e.g., coverings and/or paddings for sun visors, speaker housings and coverings, seat coverings, seal slip agents, and backings for seat coverings, carpeting and carpet reinforcement including carpet backing, car mats and backings for car mats, coverings for seat belts and seat belt anchorages, trunk floor coverings and liners, rear shelf panels, headliner facings and backings, upholstery backings, general decorative fabrics, etc.), materials that can provide general temperature and/or noise insulation (e.g., column padding, door trim pads, hood liners, general sound proofing and insulation materials, muffler wraps, bodywork parts, windows, saloon roofs, and sunroofs, tire reinforcements, etc.), and filtration/engine materials (e.g., fuel filters, oil filters, battery separators, cabin air filters, transmission tunnel materials, fuel tanks, etc.).

Solid moldings including the polyolefin material can be utilized to enhance automotive safety components. For instance, the polyolefin material can be encompassed in passive safety components such as crumple zones on the rear, front, and/or sides of a vehicle; within the safety cell of the automobile, as a component of the airbag or steering wheel (e.g., a collapsible steering column); as a cargo barrier; or as a component of a pedestrian safety system (e.g., as a component of the bumpers, hood, window frame, etc.).

The low density of the polyolefin material can provide weight saving benefits in automotive applications. For example, the polyolefin material can be a component of the structure of an automobile including, without limitation, the hood, bumpers and/or bumper supports, the trunk lid and/or compartment, and the underbody of the vehicle.

Such broad-based application of the polyolefin material is applicable to a wide variety of fields, and is not intended to be in any way limited to the automotive industry. For instance, the polyolefin material can be used in the transportation industry in any suitable application including, without limitation, air and space applications (e.g., airplanes, helicopters, space transports, military aerospace devices, etc.), marine applications (boats, ships, recreational vehicles), trains, and so forth. The polyolefin material can be utilized in transportation applications in any desired fashion, e.g., in fibrous articles or solid moldings, in aesthetic applications, for temperature and/or noise insulation, in filtration and/or engine components, in safety components, etc.

The present invention may be better understood with reference to the following examples.

Test Methods

Melt Flow Rate:

The melt flow rate ("MFR") is the weight of a polymer (in grams) forced through an extrusion rheometer orifice (0.0825-inch diameter) when subjected to a load of 2160 grams in 10 minutes, typically at 190° C., 210° C., or 230° C. Unless otherwise indicated, melt flow rate is measured in accordance with ASTM Test Method D1238 with a Tinius Olsen Extrusion Plastometer.

Thermal Properties:

The glass transition temperature ($T_g$) may be determined by dynamic mechanical analysis (DMA) in accordance with ASTM E1640-09. A Q800 instrument from TA Instruments may be used. The experimental runs may be executed in tension/tension geometry, in a temperature sweep mode in the range from −120° C. to 150° C. with a heating rate of 3° C./min. The strain amplitude frequency may be kept constant (2 Hz) during the test. Three (3) independent samples may be tested to get an average glass transition temperature, which is defined by the peak value of the tan δ curve, wherein tan δ is defined as the ratio of the loss modulus to the storage modulus (tan δ=E"/E').

The melting temperature may be determined by differential scanning calorimetry (DSC). The differential scanning calorimeter may be a DSC Q100 Differential Scanning Calorimeter, which was outfitted with a liquid nitrogen cooling accessory and with a UNIVERSAL ANALYSIS 2000 (version 4.6.6) analysis software program, both of which are available from T.A. Instruments Inc. of New Castle, Del. To avoid directly handling the samples, tweezers or other tools are used. The samples are placed into an aluminum pan and weighed to an accuracy of 0.01 milligram on an analytical balance. A lid is crimped over the material sample onto the pan. Typically, the resin pellets are placed directly in the weighing pan.

The differential scanning calorimeter is calibrated using an indium metal standard and a baseline correction is performed, as described in the operating manual for the differential scanning calorimeter. A material sample is placed into the test chamber of the differential scanning calorimeter for testing, and an empty pan is used as a reference. All testing is run with a 55-cubic centimeter per minute nitrogen (industrial grade) purge on the test chamber. For resin pellet samples, the heating and cooling program is a 2-cycle test that began with an equilibration of the chamber to −30° C., followed by a first heating period at a heating rate of 10° C. per minute to a temperature of 200° C., followed by equilibration of the sample at 200° C. for 3 minutes, followed by a first cooling period at a cooling rate of 10° C. per minute to a temperature of −30° C., followed by equilibration of the sample at −30° C. for 3 minutes, and then a second heating period at a heating rate of 10° C. per minute to a temperature of 200° C. All testing is run with a 55-cubic centimeter per minute nitrogen (industrial grade) purge on the test chamber.

The results are evaluated using the UNIVERSAL ANALYSIS 2000 analysis software program, which identified and quantified the glass transition temperature ($T_g$) of inflection, the endothermic and exothermic peaks, and the areas under the peaks on the DSC plots. The glass transition temperature is identified as the region on the plot-line where a distinct change in slope occurred, and the melting temperature is determined using an automatic inflection calculation.

Molded Article Tensile Properties:

Modulus may be determined utilizing a MTS 810 hydraulic tensile frame to pull injection molded Type I dog bones as described in ASTM D638-10 (specimens pulled at a rate of 50 mm/min or 87.7%. min deformation). The tensile frame grips may be at a nominal gage length of 115 mm. Peak stress, break stress, elongation at break, and energy per volume at break may be determined using a MTS Synergie 200 tensile frame to pull injection molded Type V dog bones at described in ASTM D638-10 (specimens may be pulled at a rate of 8.4 mm/min or 87.7%/min deformation). The tensile frame grips may be at a nominal gage length of 25.4 mm. In each test, the specimens may be conditioned at 23° C.±2° C. and 50%±10% relative humidity for not less than 40 hours. Test conditions may be at 23° C.±2° C. and 50%±10% relative humidity. Five (5) specimens may be tested for each composition. A computer program (e.g., TestWorks 4) may be used to collect data during testing and to generate a stress versus strain curve from which the average modulus, peak stress, break stress, elongation at break, and energy per volume at break may be determined.

Film Tensile Properties:

Films may be tested for tensile properties (peak stress, modulus, strain at break, and energy per volume at break) on a MTS Synergie 200 tensile frame. The test may be performed in accordance with ASTM D638-10 (at about 23° C.). Film samples may be cut into dog bone shapes with a center width of 3.0 mm before testing. The dog-bone film samples may be held in place using grips on the MTS Synergie 200 device with a gauge length of 18.0 mm. The film samples may be stretched at a crosshead speed of 5.0 in/min until breakage occurred. Five samples may be tested for each film in both the machine direction (MD) and the cross direction (CD). A computer program (e.g., TestWorks 4) may be used to collect data during testing and to generate a stress versus strain curve from which a number of properties may be determined, including modulus, peak stress, elongation, and energy to break.

Fiber Tensile Properties:

Fiber tensile properties may be determined in accordance with ASTM 638-10 at 23° C. For instance, individual fiber specimens may initially be shortened (e.g., cut with scissors) to 38 millimeters in length, and placed separately on a black velvet cloth. 10 to 15 fiber specimens may be collected in this manner. The fiber specimens may then be mounted in a substantially straight condition on a rectangular paper frame having external dimension of 51 millimeters×51 millimeters and internal dimension of 25 millimeters×25 millimeters. The ends of each fiber specimen may be operatively attached to the frame by carefully securing the fiber ends to the sides of the frame with adhesive tape. Each fiber specimen may be measured for its external, relatively shorter, cross-fiber dimension employing a conventional laboratory microscope, which may be properly calibrated and set at 40× magnification. This cross-fiber dimension may be recorded as the diameter of the individual fiber specimen. The frame helps to mount the ends of the sample fiber specimens in the upper and lower grips of a constant rate of extension type tensile tester in a manner that avoids excessive damage to the fiber specimens.

A constant rate of extension type of tensile tester and an appropriate load cell may be employed for the testing. The load cell may be chosen (e.g., 10N) so that the test value falls within 10-90% of the full scale load. The tensile tester (i.e., MTS SYNERGY 200) and load cell may be obtained from MTS Systems Corporation of Eden Prairie, Mich. The fiber specimens in the frame assembly may then be mounted between the grips of the tensile tester such that the ends of the fibers may be operatively held by the grips of the tensile tester. Then, the sides of the paper frame that extend parallel to the fiber length may be cut or otherwise separated so that the tensile tester applies the test force only to the fibers. The fibers may be subjected to a pull test at a pull rate and grip speed of 12 inches per minute. The resulting data may be analyzed using a TESTWORKS 4 software program from the MTS Corporation with the following test settings:

| Calculation Inputs | | Test Inputs | |
|---|---|---|---|
| Break mark drop | 50% | Break sensitivity | 90% |
| Break marker elongation | 0.1 in | Break threshold | 10 gf |
| Nominal gage length | 1 in | Data Acq. Rate | 10 Hz |
| Slack pre-load | 1 lb$_f$ | Denier length | 9000 m |
| Slope segment length | 20% | Density | 1.25 g/cm$^3$ |
| Yield offset | 0.20% | Initial speed | 12 in/min |
| Yield segment length | 2% | Secondary speed | 2 in/min |

The tenacity values may be expressed in terms of gram-force per denier. Peak elongation (% strain at break) and peak stress may also be measured.

The peak load of a web may be determined using a 2"×6" strip cut along the length (MD) and width direction(CD). The test may be performed in a universal tensile tester equipped with two 1"×3" rubber coated grips. The gauge length may be 76 t 1 mm (3±0.04").

Density and Percent Void Volume:

To determine density and percent void volume, the width ($W_i$) and thickness ($T_i$) of the specimen may be initially measured prior to drawing. The length ($L_i$) before drawing may also be determined by measuring the distance between two markings on a surface of the specimen. Thereafter, the specimen may be drawn to initiate pore formation. The width ($W_f$), thickness ($T_f$), and length ($L_f$) of the specimen may then be measured to the nearest 0.01 mm utilizing Digimatic Caliper (Mitutoyo Corporation). The volume ($V_i$) before drawing may be calculated by $W_i \times T_i \times L_i = V_i$. The volume ($V_f$) after drawing may also be calculated by $W_f \times T_f \times L_f = V_f$. The density ($P_f$) may be calculated by $P_f = P_i/\varphi$, where $P_i$ is density of precursor material and the percent void volume (% $V_v$) was calculated by: % $V_v = (1 - 1/\varphi) \times 100$.

Hydrostatic Pressure Test ("Hydrohead"):

The hydrostatic pressure test is a measure of the resistance of a material to penetration by liquid water under a static pressure and is performed in accordance with AATCC Test Method 127-2008. The results for each specimen may be averaged and recorded in centimeters (cm). A higher value indicates greater resistance to water penetration.

Water Vapor Transmission Rate ("WVTR")

The test used to determine the WVTR of a material may vary based on the nature of the material. One technique for measuring the WVTR value is ASTM E96/96M-12, Procedure B. Another method involves the use of INDA Test Procedure IST-70.4 (01). The INDA test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modem Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow that is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer then calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material, guardfilm, airgap} - TR^{-1}_{guardfilm, airgap}$$

The water vapor transmission rate ("WVTR") is then calculated as follows:

$$WVTR = \frac{F\rho_{sat(T)}RH}{AP_{sat(T)}(1-RH)}$$

wherein,

F=the flow of water vapor in cm³ per minute;

$\rho_{sat(T)}$=the density of water in saturated air at temperature T;

RH=the relative humidity at specified locations in the cell;

A=the cross sectional area of the cell; and $P_{sat(T)}$=the saturation vapor pressure of water vapor at temperature T.

Conductive Properties

Thermal conductivity (W/mK) and thermal resistance (m²K/W) may be determined in accordance with ASTM E-1530-11 ("Resistance to Thermal Transmission of Materials by the Guarded Heat Flow Meter Technique") using an Anter Unitherm Model 2022 tester. The target test temperature may be 25° C. and the applied load may be 0.17 MPa. Prior to testing, the samples may be conditioned for 40+ hours at a temperature of 23° C. (±2° C.) and relative humidity of 50% (±10%). Thermal admittance (W/m²K) may also be calculated by dividing 1 by the thermal resistance.

Frazier Porosity:

The Frazier porosity was measured in a Frazier® Low Differential Pressure Air Permeability Tester (FAP-LP) by cutting an 8" strip (measured along the machine direction) of a sample and folding the sample accordion style (in the cross direction) to obtain six layers.

Example 1

A precursor blend was made that contained 95 wt. % isotactic propylene homopolymer (M3661, melt flow rate of 14 g/10 at 230° C. and melting temperature of 150° C., Total Petrochemicals) in combination with 5 wt. % alkoxylated alcohol (Pluriol® WI 285, BASF). The components were compounded in a co-rotating twin-screw extruder (Werner and Pfleiderer ZSK-30 with a diameter of 30 mm and a L/D=44). The extruder had seven heating zones. The temperature in the extruder ranged from 180° C. to 220° C. The polymer was fed gravimetrically to the extruder at the hoper at 15 pounds per hour and the liquid was injected into the barrel using a peristaltic pump. The extruder was operated at 200 revolutions per minute (RPM). In the last section of the barrel (front), a 3-hole die of 6 mm in diameter was used to form the extrudate. The extrudate was air-cooled in a conveyor belt and pelletized using a Conair Pelletizer. Injection molded specimens (ASTM D638 Type 1) were made of the precursor blend using a Boy 22D injection molding machine with 3 heating sections. The temperature in the heating sections ranged from 185 to 220° C. The injection holding pressure time ranged from 14 s to 24 s, the cooling time from 12 to 23 s, cycle time ranged from 22 s to 43 s, and the mold temperature was set at about 21° C.

Figure 2:
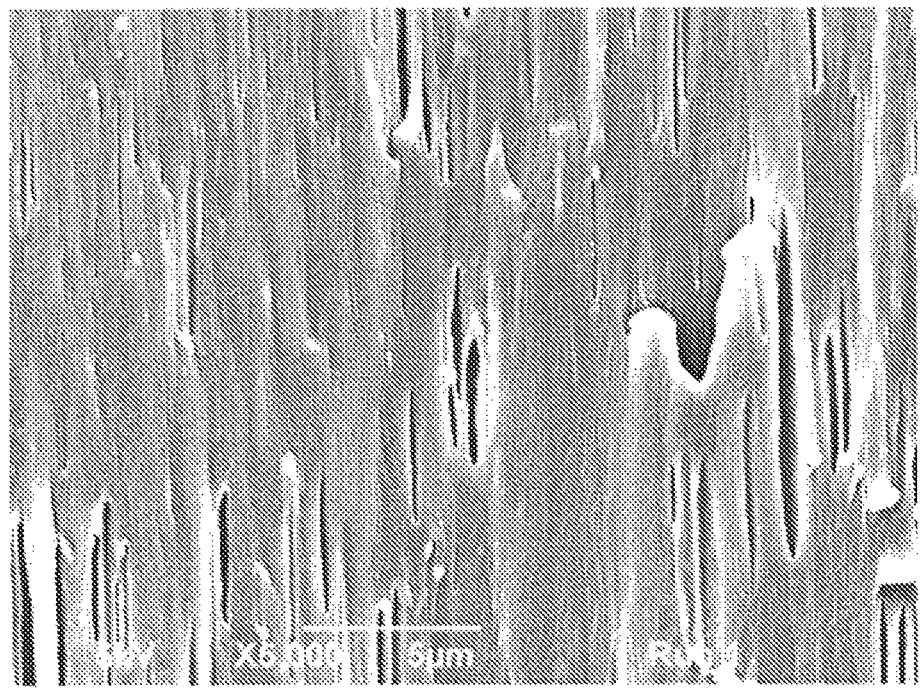
FIG. 2 is an SEM photomicrograph of the stretched injection molded sample of Example 1 (polypropylene and alkoxylated alcohol) after freeze fracturing in liquid nitrogen.

Once formed, the molded specimens were stretched in an 810 Material Test System tension tester at a cross-head speed of 25 mm/min at 25° C. To analyze the material morphology, both the unstretched and stretched injection molded bars were freeze fractured in liquid nitrogen. The fractured surfaces were sputter coated with gold-palladium alloy, and analyzed via Scanning Electron Microscope Jeol 6490LV at high vacuum. The results are shown in FIG. 1. As shown in FIG. 1, Pluriol® WI 285 can initially form liquid nanodomains in the polypropylene matrix that have a width of about 50 to 500 nanometers. FIG. 2 shows an example of the freeze fractured surface of the stretched molded bar containing liquid domains, viewed perpendicular to the long axis of the necked area. As shown, a porous network is formed in the polypropylene matrix that contains nanopores having a width of 100 to 500 nanometers and length of 2 to 5 micrometers.

Example 2

Figure 3:
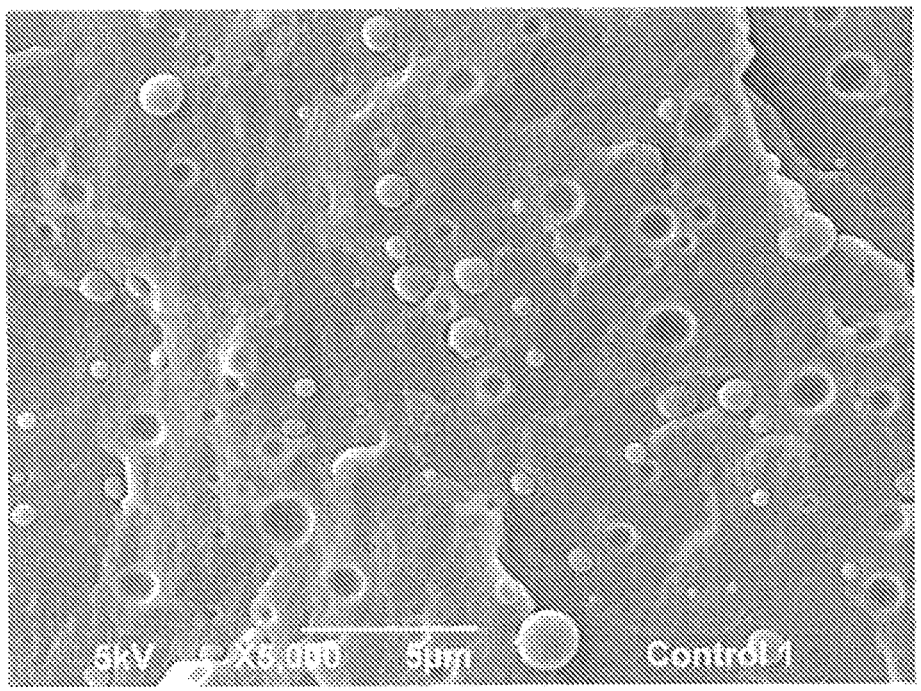
FIG. 3 is an SEM photomicrograph of the unstretched stretched injection molded sample of Example 2 (polypropylene and polylactic acid) after freeze fracturing in liquid nitrogen.
Figure 4:
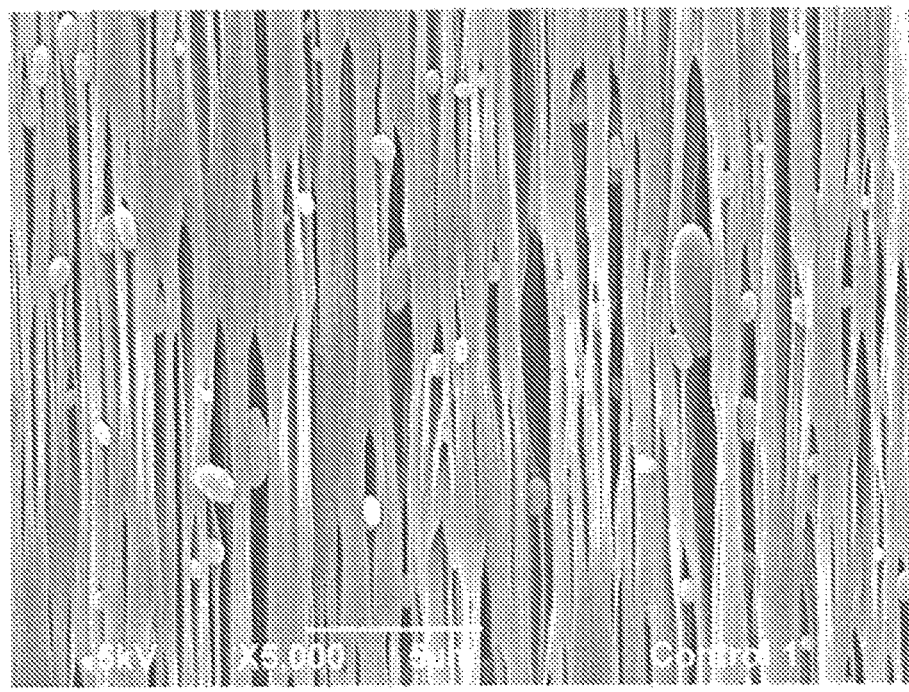
FIG. 4 is an SEM photomicrograph of the stretched stretched injection molded sample of Example 2 (polypropylene and polylactic acid) after freeze fracturing in liquid nitrogen.
Figure 5:
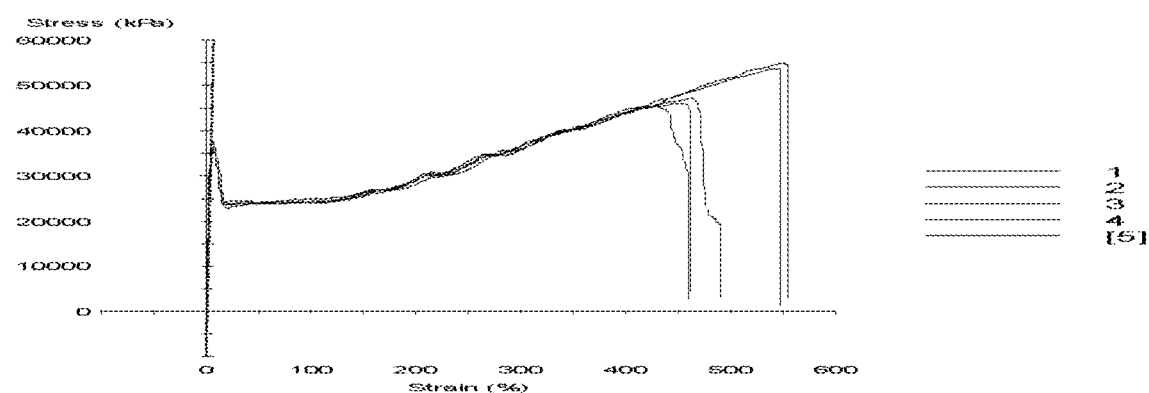
FIG. 5 is a stress-strain curve for the stretched sample of Example 2.

A precursor blend was formed from 92.5% wt. % polypropylene (M3661, Total Petrochemicals) and 7.5 wt. % polylactic acid (PLA 6252, melt flow rate of 70 to 85 g/10 min at 210° C., Natureworks®) in the manner described in Example 1. Injection molded specimens were also formed and tested before and after stretching as described in Example 1. The results are shown in FIGS. 3-4. As indicated in FIG. 3, the blend exhibited a relatively large domain size. Upon stretching, as shown in FIG. 4, the larger domain sizes of the blend tended to form relatively long and wide pores. A stress-strain curve was also generated for the stretched sample and is shown in FIG. 5. As shown, the blend showed a premature and random failure.

Example 3

Figure 6:
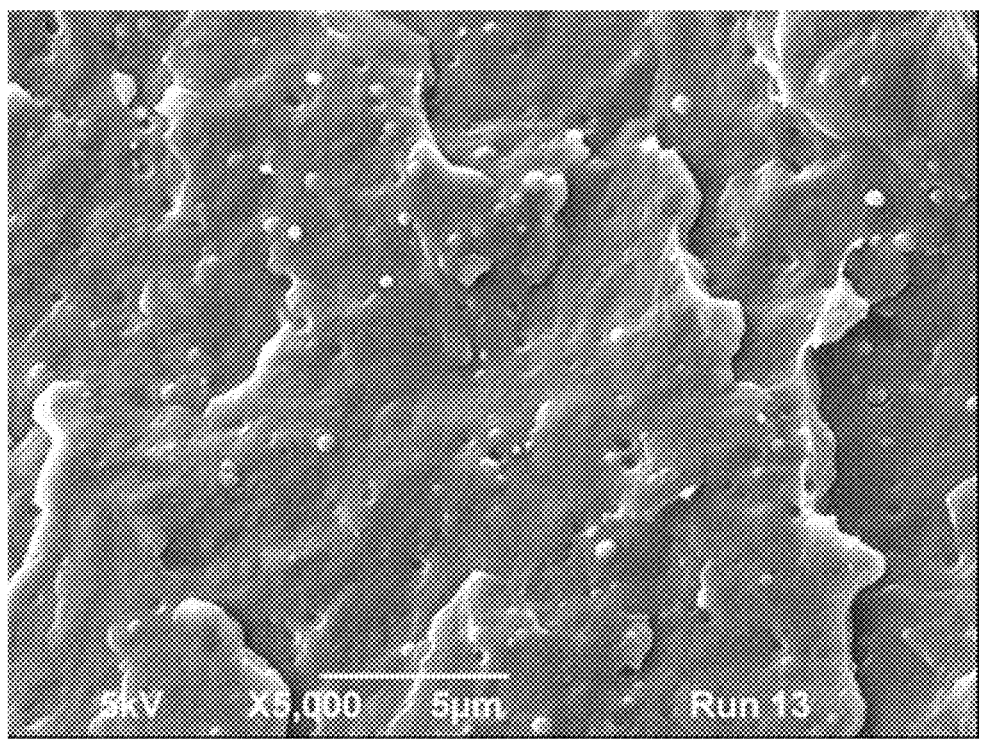
FIG. 6 is an SEM photomicrograph of the unstretched injection molded sample of Example 3 (polypropylene, polylactic acid, and polyepoxide) after freeze fracturing in liquid nitrogen.
Figure 7:
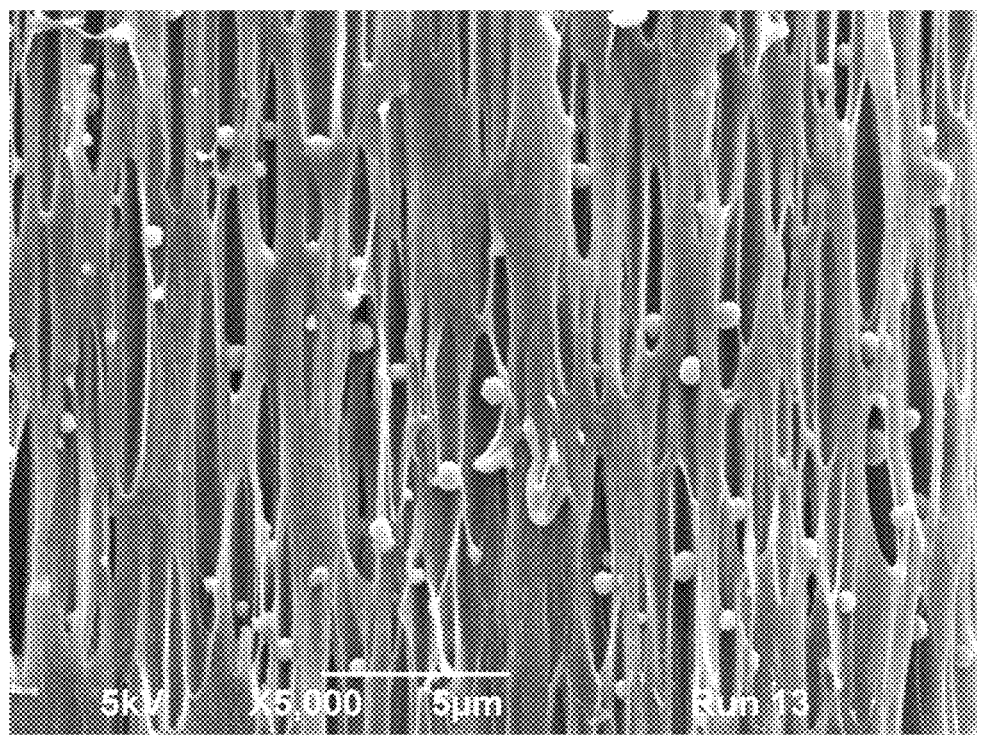
FIG. 7 is an SEM photomicrograph of the stretched injection molded sample of Example 3 (polypropylene, polylactic acid, and polyepoxide) after freeze fracturing in liquid nitrogen.
Figure 8:
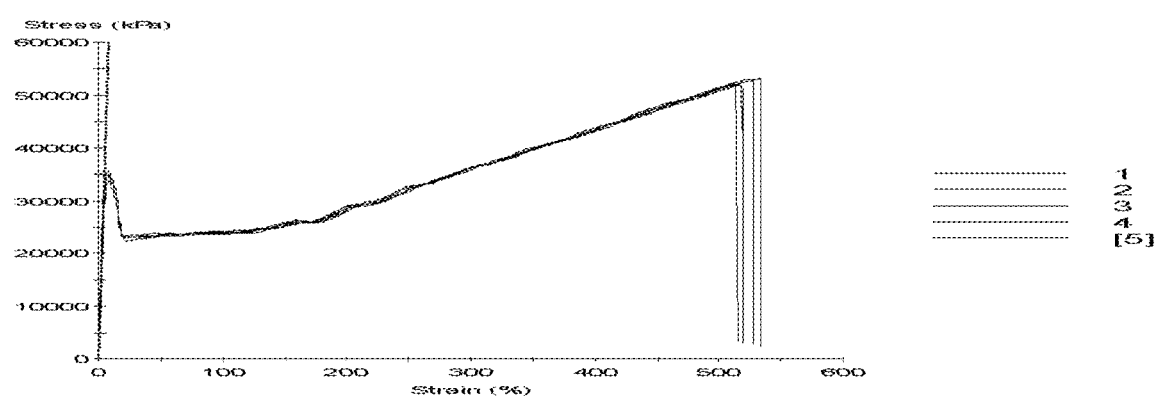
FIG. 8 is a stress-strain curve for the stretched sample of Example 3.

A precursor blend was formed from about 91.8 wt. % polypropylene (M3661, Total Petrochemicals) 7.4 wt. % PLA 6252, and 0.7 wt. % of a polyepoxide in the manner described in Example 1. The polyepoxide was poly(ethylene-co-methyl acrylate-co-glycidyl methacrylate) (LOTADER® AX8900, Arkema) having a melt flow rate of 6 g/10 min (190° C./2160 g), a glycidyl methacrylate content of 8 wt. %, methyl acrylate content of 24 wt. %, and ethylene content of 68 wt. %. Injection molded specimens were also formed and tested before and after stretching as described in Example 1. The results are shown in FIGS. 6-7. As indicated in FIG. 6, the blend exhibited a relatively small domain size. Upon stretching, as shown in FIG. 7, the small domain sizes of the blend tended to form relatively small pores. A stress-strain curve was also generated for the stretched sample and is shown in FIG. 8. As shown, the blend showed good mechanical properties, similar to that of neat polypropylene. Also, a section of the necked region of the stretched molded bar was cut and then submerged in hexane (density of 0.65 g/cc). It was observed that the necked region of the stretched molded bars floated in hexane, which suggested that the density is lower than 0.65 g/cc.

Example 4

Figure 9:
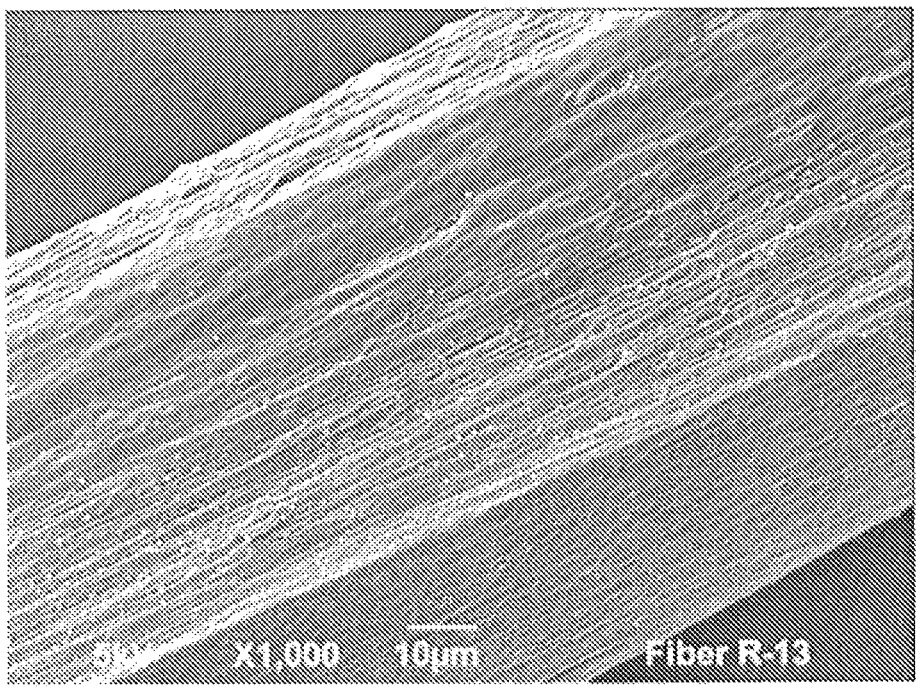
FIG. 9 is an SEM photomicrograph (1,000×) of the fiber of Example 4 (polypropylene, polylactic acid, and polyepoxide) after freeze fracturing in liquid nitrogen.
Figure 10:
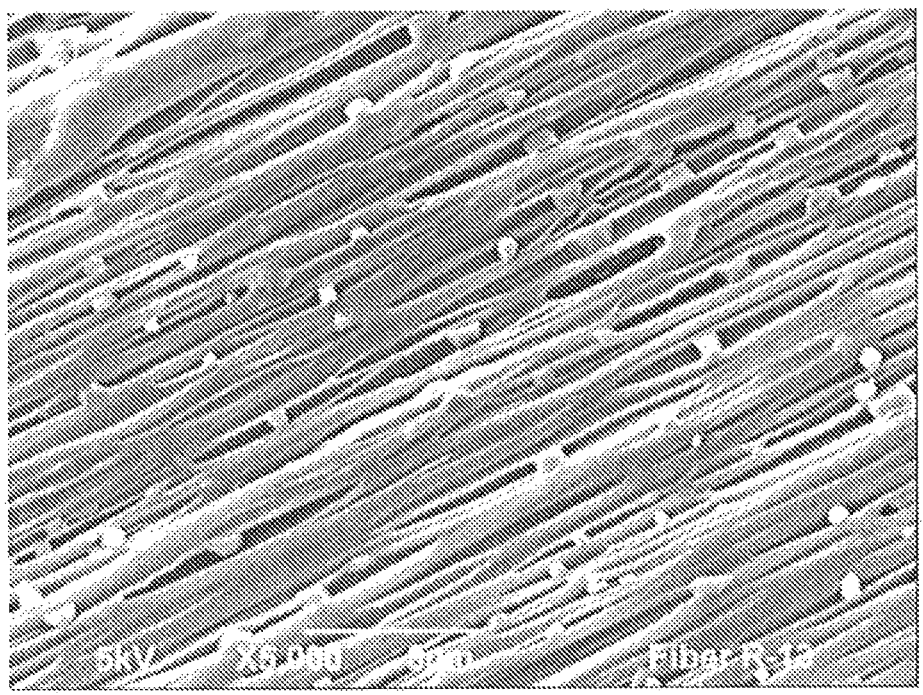
FIG. 10 is an SEM photomicrograph (5,000×) of the fiber of Example 4 (polypropylene, polylactic acid, and polyepoxide) after freeze fracturing in liquid nitrogen.
Figure 11:
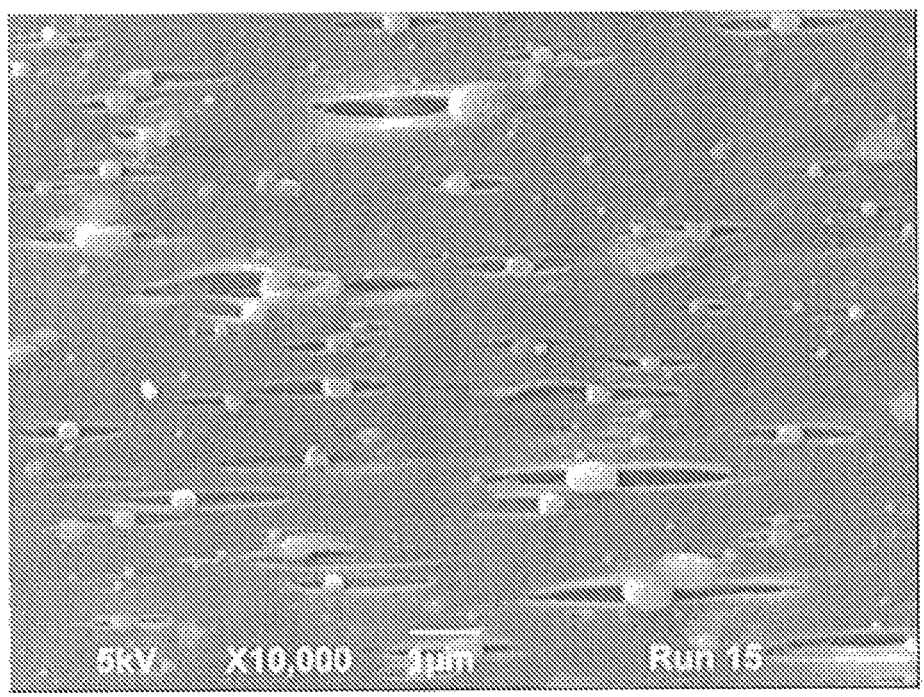
FIG. 11 is an SEM photomicrograph (10,000×) of the fiber surface of Example 4 (polypropylene, polylactic acid, and polyepoxide)

Fiber was produced from the precursor blend of Example 3 using a Davis-Standard fiber spinning line equipped with a 0.75-inch single screw extruder and 16 hole spinneret with a diameter of 0.6 mm. The fibers were collected at different draw down ratios. The take up speed ranged from 1 to 1000 m/min. The temperature of the extruder ranged from 175° C. to 220° C. The fibers were stretched in a tensile tester machine at 300 mm/min up to 400% elongation at 25° C. To analyze the material morphology, the fibers were freeze fractured in liquid nitrogen and analyzed via Scanning Electron Microscope Jeol 6490LV at high vacuum. The results are shown in FIG. 9-11. As shown, spheroidal pores are formed that are highly elongated in the stretching direction. Both nanopores (~50 nanometers in width, ~500 nanometers in length) and micropores (~0.5 micrometers in width, ~4 micrometers in length) were formed.

Example 5

A blend of 93 wt. % polypropylene (Total M3661) and 7 wt. % Lotader® AX8900) were compounded in a co-rotating twin-screw extruder (Werner and Pfleiderer ZSK-30 with a diameter of 30 mm and a L/D=44). The extruder had seven heating zones. The temperature in the extruder ranged from 180° C. to 220° C. The polymer was feed gravimetrically to the extruder at the hoper at 15 pounds per hour. The extruder was operated at 200 revolutions per minute (RPM). In the last section of the barrel (front), a 3-hole die of 6 mm in diameter was used to form the extrudate. The extrudate was air-cooled in a conveyor belt and pelletized using a Conair Pelletizer. Injection molded specimens (ASTM D638 Type 1) were obtained in a Boy 22D Injection molding machine with 3 heating sections. The temperature of the heating sections ranged from 185 to 220° C. To analyze the material morphology, the unstretched molded bars were cut with a razor blade and the cross sectional area was polished using aluminum oxide polishing discs having a size from 1 to 0.05 microns. To extract the Lotader® AX8900, the polished specimens were soaked in chloroform for 12 hours.

Figure 12:
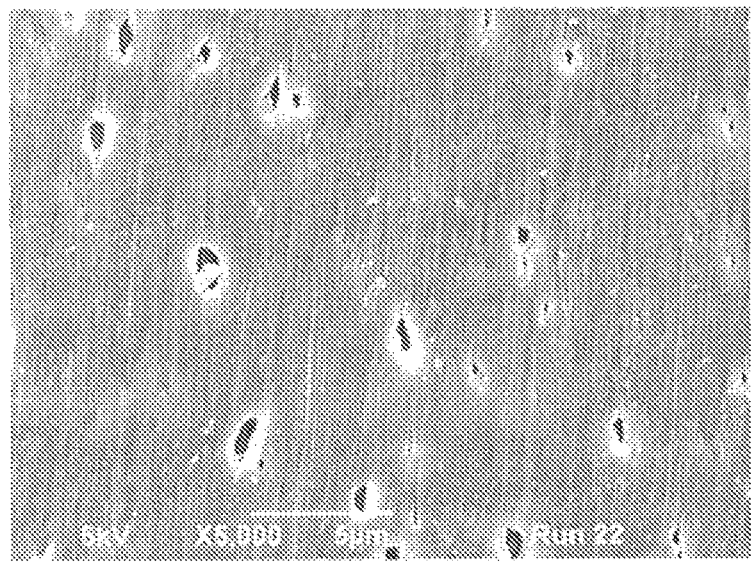
FIG. 12 is an SEM photomicrograph (5,000×) of the cross-sectional area (polished and etched with chloroform) of the injection molded bar of Example 5.
Figure 13:
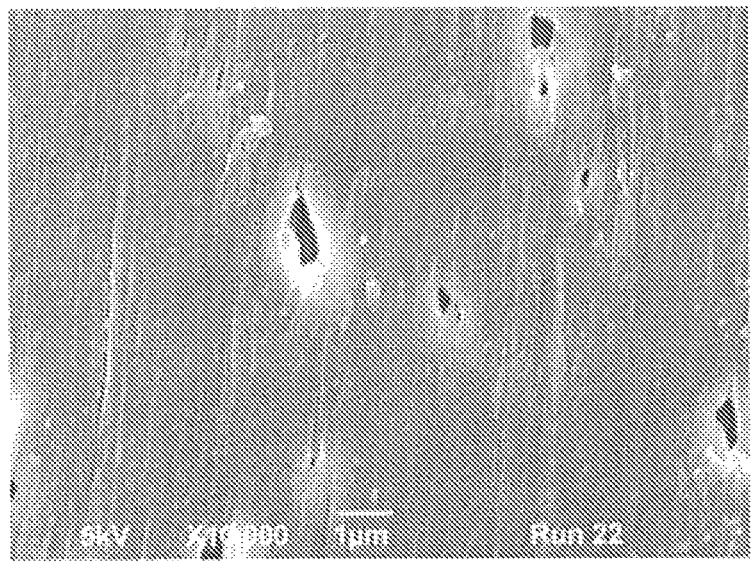
FIG. 13 is an SEM photomicrograph (10,000×) of the cross-sectional area (polished and etched with chloroform) of the injection molded bar of Example 5.
Figure 14:
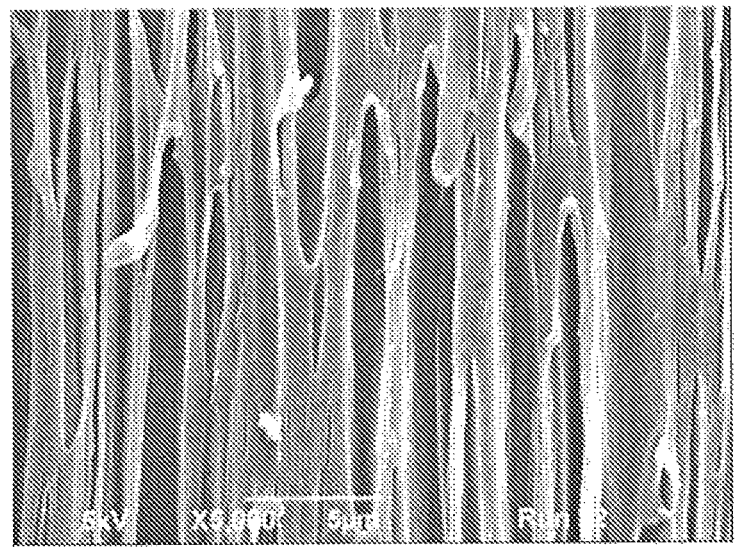
FIG. 14 is an SEM photomicrograph (5,000×) of the freeze-fractured necked region along the axial direction of the stretched injection molded bar of Example 5.
Figure 15:
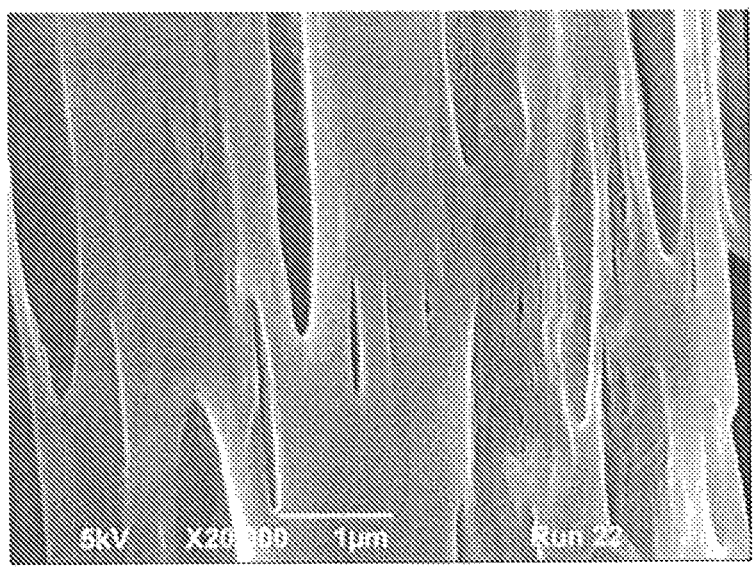
FIG. 15 is an SEM photomicrograph (20,000×) of the freeze-fractured necked region along the axial direction of the stretched injection molded bar of Example 5.

The results are shown in FIGS. 12-15. FIGS. 12-13 show the polished surface of the PPM3661/Lotader® AX8900 blend. The cavities observed in the polished surface correspond to the spaces that were occupied by the Lotader® domains. The necked region of the stretched injection molded bars were also freeze fractured in liquid nitrogen. The surfaces were sputter coated with gold-palladium alloy and analyzed via Scanning Electron Microscope Jeol 6490LV at high vacuum. FIGS. 14-15 show the freeze-fractured necked region along the axial direction of the stretched injection molded bar.

Example 6

Figure 16:
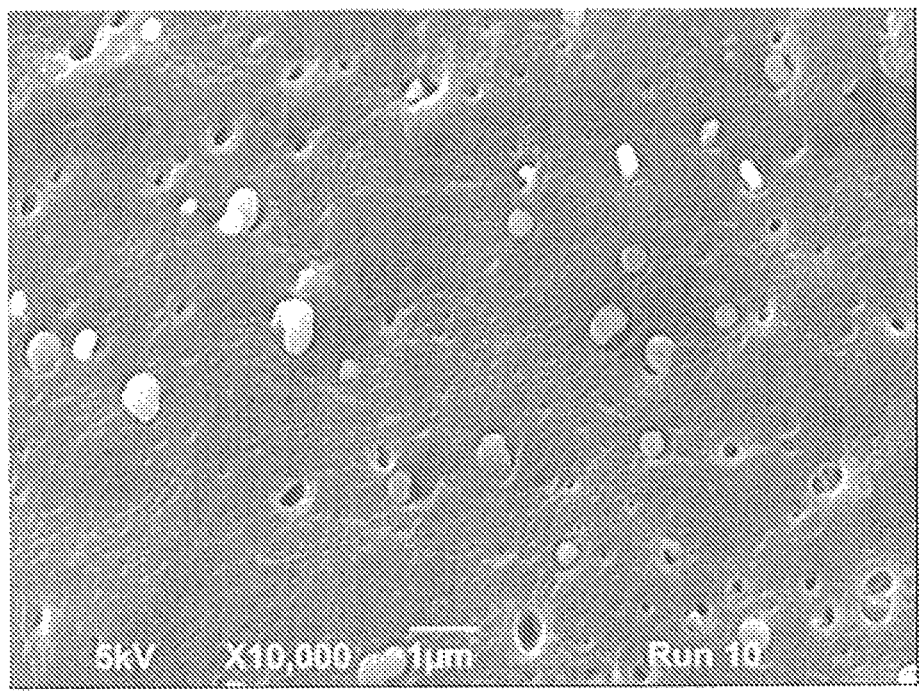
FIG. 16 is an SEM photomicrograph (10,000×) of the freeze-fractured cross-sectional area of the un-stretched molded bar of Example 6.
Figure 17:
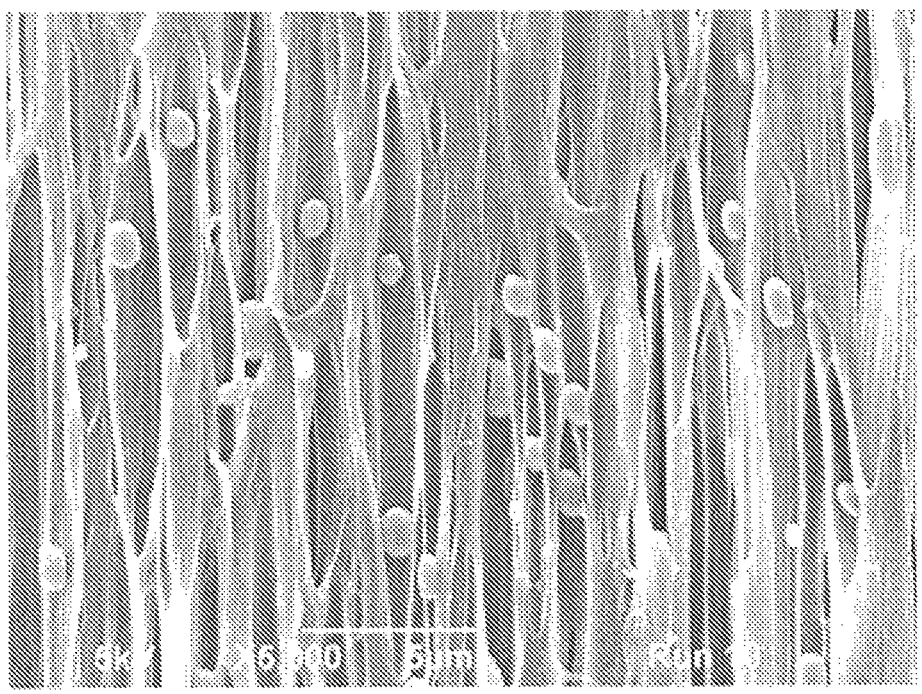
FIG. 17 is an SEM photomicrograph (5,000×) of the freeze-fractured cross-sectional area along the axial dimension of the stretched molded bar of Example 6.

A blend of 91.1 wt. % polypropylene (Total M3661), 7.4 wt. % polylactic acid (NatureWorks 6251), and 1.5% Lotader® AX8900) were compounded in the extruder and the conditions described in Example 5. In this case, 5% of Pluriol® WI 285 was then injected to the barrel using a peristaltic pump. Injection molded bars were prepared as described above. The unstretched bars and the neck region of the stretched bars were freeze-fractured in liquid nitrogen. The fractured surfaces were sputter coated with gold-palladium alloy, and analyzed via Scanning Electron Microscope Jeol 6490LV at high vacuum. The results are set forth in FIGS. 16-17.

Example 7

A blend of materials was formed that contained 91.5 wt. % polypropylene (Total Petrochemicals M-3661), 7.5 wt. % polylactic acid (Natureworks Ingeo 6251D), and 1.0 wt. % of a polyepoxide modifier (Arkema Lotader AX8900). This mixture was then melt blended via a twin screw extruder at 220° C. to form a homogeneous polymer blend. The molten polymer blend was extruded through a multi-filament die, quenched via water, and cut in to a pellet via underwater pelletizing system such as those available from Gala Industries of Eagle Rock, Va. The compounded pellet was then flood fed into a single screw extruder (24:1 length to diameter ratio) with a cast film die. Materials were melted at a temperature of 220° C. and extruded through a film die on to a casting roll at a temperature of 25° C. A melt draw force was applied to the molten film to reduce the thickness to approximately 177 to 203 micrometers.

Example 8

A film was formed as described in Example 7, except that the thickness was 254 to 279 micrometers.

Example 9

The film of Example 7 was solid state drawn in a tensile frame (e.g., Sintech 1/S frame available from MTS systems) at a rate of 50 millimeters per minute to a strain of 300%. After stretching, it was determined that the length of the film increased 5.2 times in the machine direction and the width of the film decreased by 20%.

Example 10

Figure 18:
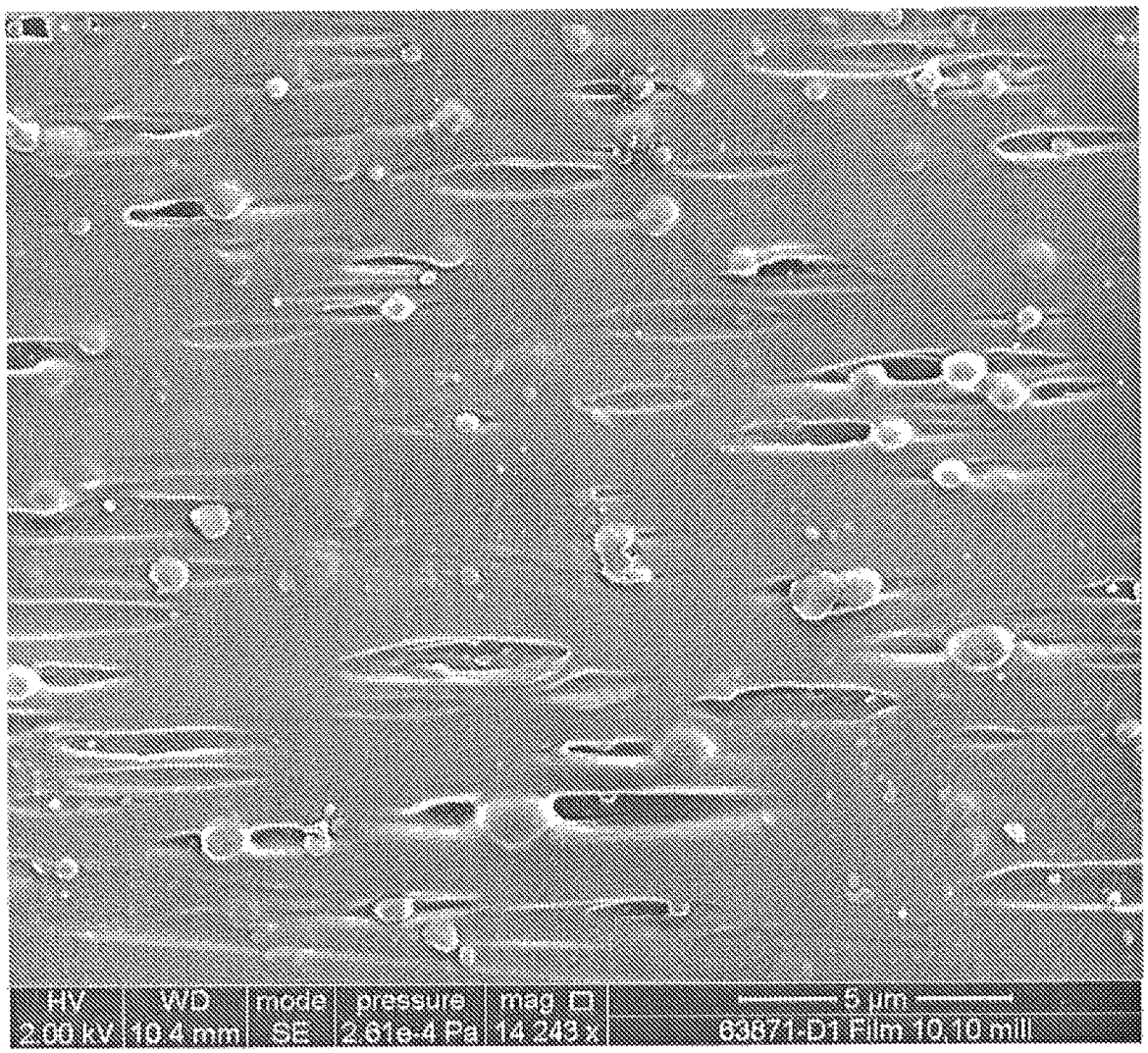
FIG. 18 is an SEM microphotograph of a surface of the film of Example 10 taken at a magnification of 14,243×.
Figure 19:
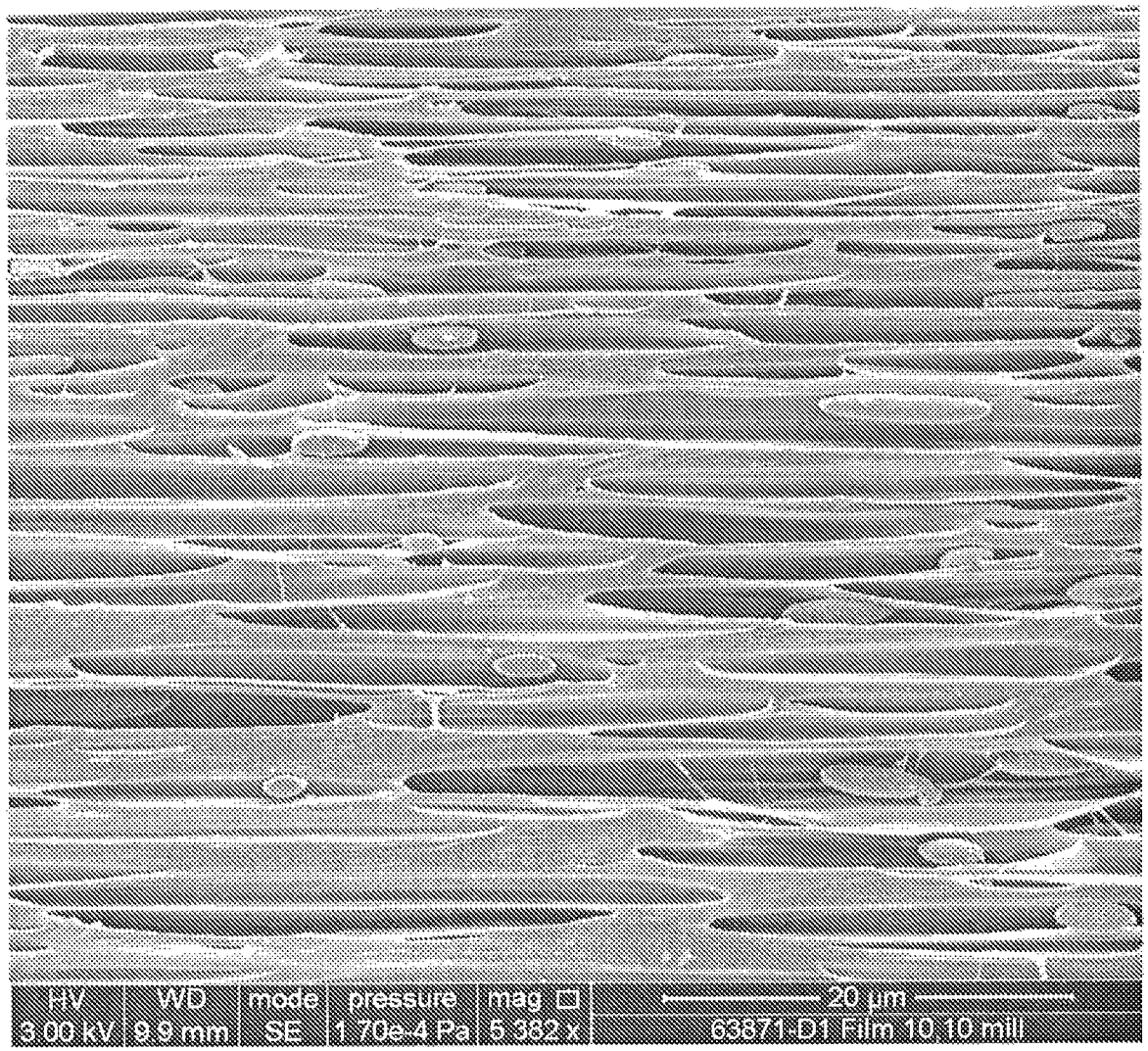
FIG. 19 is an SEM microphotograph of the film of Example 10 (cut in machine direction plane) taken at a magnification of 5,382×.

The film of Example 8 was solid state drawn in a tensile frame (e.g., Sintech 1/S frame available from MTS systems) at a rate of 50 millimeters per minute to a strain of 300%. After stretching, it was determined that the length of the film increased 5.6 times in the machine direction and the width of the film decreased by 20%. SEM microphotographs of the film are shown in FIGS. 18-19.

Various mechanical properties of the drawn films of Examples 9 and 10 were tested. The results are set forth in the table below.

|  | Thickness (μm) | Modulus (MPa) | Break Stress (MPa) | Strain at Break (%) |
| --- | --- | --- | --- | --- |
| Example 9 |  |  |  |  |
| MD | 64 | 3,480 | 156.9 | 19.2 |
| CD | 84 | 808 | 13.1 | 154.6 |
| Example 10 |  |  |  |  |
| MD | 84 | 3,452 | 160.3 | 15.9 |
| CD | 103 | 665 | 14.2 | 172.8 |

Example 11

A film was formed as described in Example 7, except that the thickness was 48 to 55 micrometers.

Example 12

A blend of materials was formed that contained 78 wt. % polypropylene (Total Petrochemicals M-3661), 15 wt. % polylactic acid (Natureworks Ingeo 6251D), and 7.0 wt. % of a polyepoxide modifier (Arkema Lotader AX8900). This mixture was then melt blended via a twin screw extruder at 220° C. to form a homogeneous polymer blend. The molten polymer blend was extruded through a multi-filament die, quenched via water, and cut in to a pellet via underwater pelletizing system such as those available from Gala Industries of Eagle Rock, Va. The compounded pellet was then flood fed into a single screw extruder (24:1 length to diameter ratio) with a cast film die. Materials were melted at a temperature of 220° C. and extruded through a film die on to a casting roll at a temperature of 25° C. A melt draw force was applied to the molten film to reduce the thickness to approximately 48 to 55 micrometers.

Example 13

A film was formed as described in Example 12, except that the thickness was 70 to 80 micrometers.

Example 14

A film was formed as described in Example 12, except that the thickness was 120 to 132 micrometers.

Example 15

A precursor polymer blend was made that contained 91.8 wt % of isotactic polypropylene (M3661, melt flow rate of 14 g/10 min at 230° C. and melting temperature of 150° C., Total Petrochemicals), 7.45% polylactic acid (PLA) (Ingeo 6251D, melt flow rate 70-85 g/10 at 210° C., Natureworks), and 0.75% polyepoxide compatibilizer (Arkema Lotader® AX8900). The polyepoxide modifier was poly(ethylene-co-methyl acrylate-co-glycidyl methacrylate) (Lotader® AX8900, Arkema) having a melt flow rate of 5-6 g/10 min (190° C./2160 g), a glycidyl methacrylate content of 7 to 11 wt. %, methyl acrylate content of 13 to 17 wt. %, and ethylene content of 72 to 80 wt. %. The components were compounded in a co-rotating twin screw extruder (Werner and Pfleiderer ZSK-30 with a diameter of 30 mm and a L/D=44). The extruder had seven heating zones. The temperature in the extruder ranged from 180° C. to 220° C. The polymer was fed gravimetrically to the extruder at the hoper at 6.8 Kilograms per hour (15 pounds per hour). The extruder was operated at 200 revolutions per minute (RPM). In the last section of the barrel (front), a 3-hole die of 6 mm in diameter was used to form the extrudate. The extrudate was air-cooled in a conveyor belt and pelletized using a Conair Pelletizer.

Example 16

Figure 20:
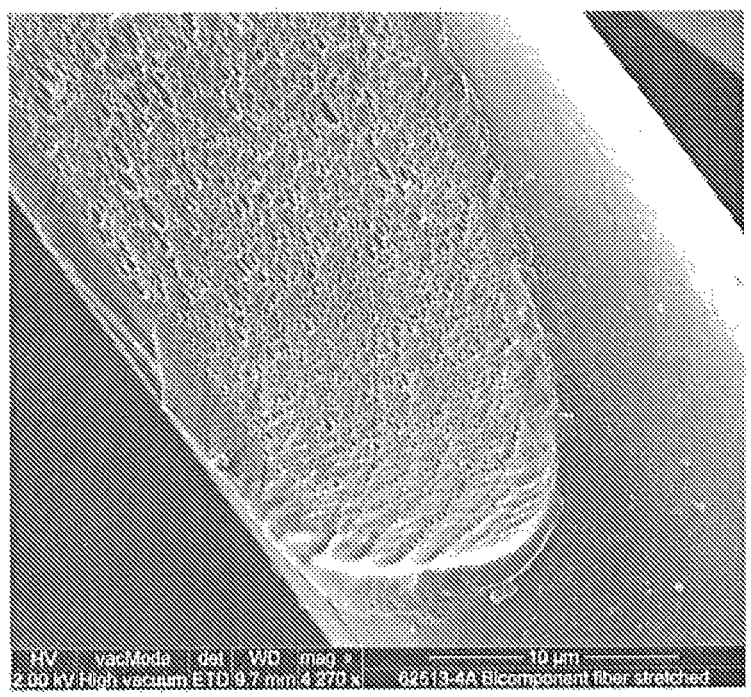
FIG. 20 is an SEM photomicrograph (4,270×) of the fiber of Example 16 after freeze fracturing in liquid nitrogen.
Figure 21:
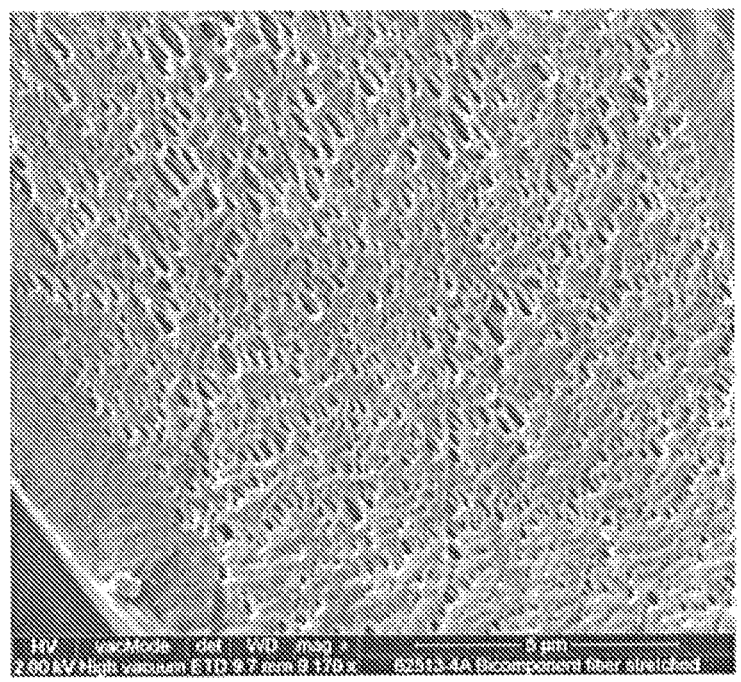
FIG. 21 is an SEM photomicrograph (9,170×) of the fiber of Example 16 after freeze fracturing in liquid nitrogen.

Bicomponent fibers were produced in a bicomponent fiber line equipped with 2 single screw extruders (1.25-in diameter). The bicomponent fiber had a 30/70, sheath/core configuration, in which the sheath was formed from 100 wt. % polypropylene (M3661, Total Petrochemicals) and the core was formed from the blend of Example 15. The extruders fed the sheath and core polymer compositions into one spinneret of 288 capillaries of 0.5 mm in diameter and 4:1 length/diameter ratio (L/D). The fibers were spun at a rate of 8 kg/hr at a spinning velocity of 660 meters per minute and collected in spools for post-stretching process. The extrusion temperature profile for both sheath and core was as follows: Zone 1=220° C., Zone 2=225° C., Zone 3=230° C., Zone 4=240° C., and Spin Beam=240° C. The melt spun fibers were then stretched at room temperature (25° C.) to 200% between two godet rolls (single step draw) at a rate of 1200 meters per minute. Then, the fibers were crimped (19 crimps per inch) and cut to a length of 38 mm. The fibers were then cut with a razor blade in liquid nitrogen and analyzed via scanning electron microscopy. The fractured surfaced were sputter-coated with gold-palladium in a Denton Vacuum Desk V sputtering system using 15 mA for 75 s and analyzed via SEM in a Field Emission Quanta 650. The results are set forth in FIGS. 20-21.

Various properties of the fibers were also tested as provided in the table below.

| | |
|---|---|
| Diameter (μm) | 19.4 |
| Tenacity (g/den) | 5.5 |
| Peak Stress (MPa) | 443.9 |
| Strain at Break (%) | 85.28 |
| Energy per volume at break (J/cm$^3$) | 269.4 |

A 100-gsm, through-air bonded carded web (TABCW) was also formed with a blend of the fibers of Example 16 (70 wt. %) and bicomponent sheath/core PE/PP fibers (30 wt. %). The web was formed in a Truetzschler High-Speed Card EWK 413 equipped with a Asselin Profile 415-FD crosslaper and a Fleissner Oven (NC State University). The carded web was through air bonded at 260° F. and the final thickness was 5.5 mm.

Example 17

Figure 22:
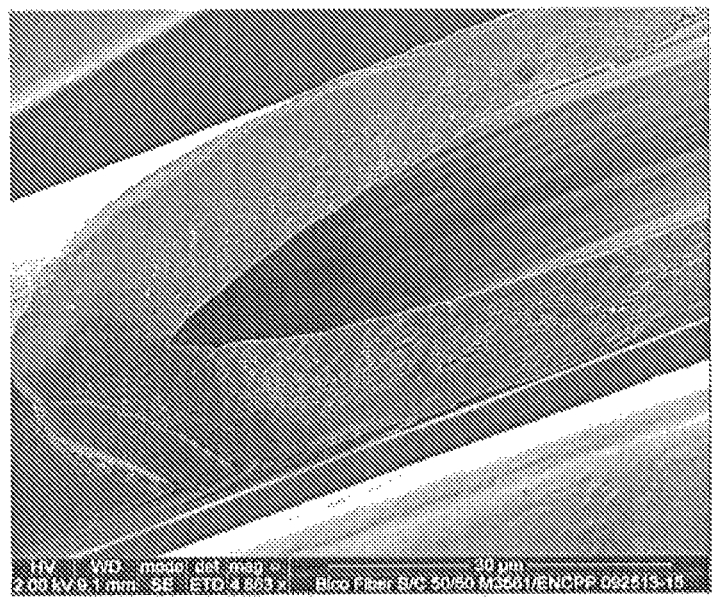
FIGS. 22-23 are SEM photomicrographs of the fiber of Example 17 after freeze fracturing in liquid nitrogen.
Figure 23:
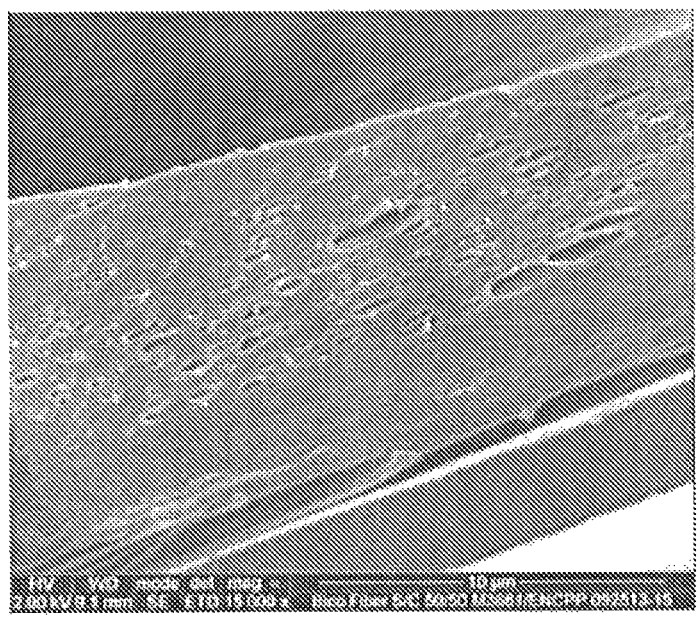

A precursor polymer blend was made as described in Example 15 that contained 93 wt % polypropylene matrix (M3661, Total Petrochemicals) and 7 wt. % of Lotader® AX8900. Hollow bicomponent fibers were produced in a bicomponent fiber line equipped with 2 single screw extruders (1.25-in diameter). The bicomponent fiber had a 50/50, sheath/core configuration, in which the sheath was formed from 100 wt. % polypropylene (Achieve 3854) and the core was formed from the blend described above. The extruders fed the sheath and core polymer compositions into one spinneret of 72 capillaries of 4 C-segments capillary design. The fibers were spun at a rate of 2 kg/hr at a spinning velocity of 198 meters per minute and collected in spools for post-stretching process. The extrusion temperature profile for both sheath and core was as follows: Zone 1=220° C., Zone 2=225° C., Zone 3=230° C., Zone 4=240® C., and Spin Beam=240® C. The fiber was quenched in a water bath located 35 cm below the spinneret. The quenched fibers were then stretched at room temperature (25° C.) to 200% between two godet rolls (single step draw) at a rate of 1200 meters per minute. The fibers were then cut with a razor blade in liquid nitrogen and analyzed via scanning electron microscopy. The fractured surfaced were sputter-coated with gold-palladium in a Denton Vacuum Desk V sputtering system using 15 mA for 75 s and analyzed via SEM in a Field Emission Quanta 650. The results are set forth in FIGS. 22-23. Various properties of the fibers were also tested as provided in the table below.

| | |
|---|---|
| Diameter (μm) | 31.4 |
| Tenacity (g/den) | 3.8 |
| Peak Stress (MPa) | 303.8 |
| Strain at Break (%) | 90.0 |
| Energy per volume at break (J/cm$^3$) | 223.1 |

Example 18

A precursor blend was formed as described in Example 15, except that the material was produced using a 64 mm co-rotating twin screw extruder at a production rate of 270 kilograms per hour (600 pounds per hour) and temperature of 220° C. The molten polymer blend was extruded through a multi-filament die, quenched via water and cut in to a pellet via underwater pelletizing system such as those available from Gala Industries of Eagle Rock, Va. A monocomponent fiber was formed from the blend at a rate of 22.5 kilograms per hour in a monocomponent fiber spinning line (FiberVisions) equipped with a 1.25 single screw extruder 24 L/D and two spinnerets, each one having 675 round capillaries (1,350 total) of 0.35 mm in diameter and 4:1 L/D ratio. The spinning speed was 435 meters per minute. The 7 extruder heating zones and the spin beam temperature profile were kept at 220° C. The spinning line was equipped with a single-sided air flow quench box and the air temperature was 21° C. The melt drawn fibers were collected in 5 pound spools with no cold drawing. The melt oriented fibers had a denier of 10.7 denier per filament.

Figure 24:
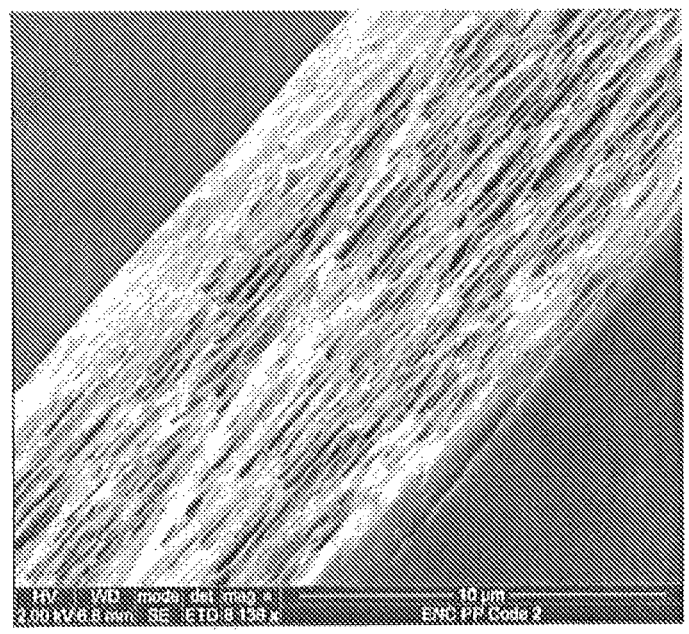
FIG. 24 is an SEM photomicrograph of the fiber of Example 18 after freeze fracturing in liquid nitrogen.

The fibers were stretched to 100% at a speed of 50 meters per minute in a stretching unit consisting of a three banks of five rolls (quintets). The temperature of the first quintet was maintained at 50° C. and the second and third quintets were maintained at a temperature of 25° C. Fibers were crimped and cut to 1.5 inches. The spin finish was adjusted before the cutting unit to 0.5%. The fibers were then cut with a razor blade in liquid nitrogen and analyzed via scanning electron microscopy. The fractured surfaced were sputter-coated with gold-palladium in a Denton Vacuum Desk V sputtering system using 15 mA for 75 s and analyzed via SEM in a Field Emission Quanta 650. The results are set forth in FIG. 24. Various properties of the fibers were also tested as provided in the table below.

| | |
|---|---|
| Diameter (μm) | 29.6 |
| Tenacity (g/den) | 3.1 |
| Peak Stress (MPa) | 244.3 |
| Strain at Break (%) | 298.8 |
| Energy per volume at break (J/cm$^3$) | 433.0 |

Figure 25:
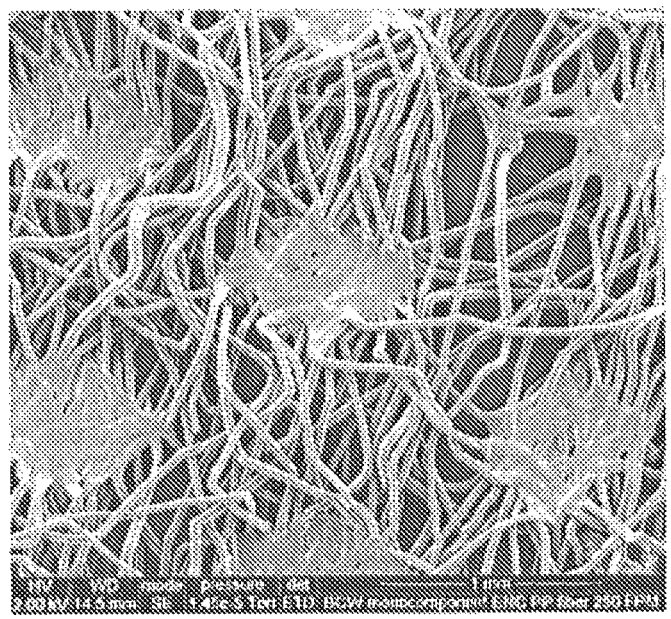
FIG. 25 is an SEM photomicrographs of the bonded web of Example 18.

Thermally bonded carded webs (30 gsm) were also produced on a carding line. To thermally bond the webs, diamond bonding pattern was used as shown in FIG. 25. The calender temperature was 150° C. and the carding speed was 250 feet per minute. Various properties of the web were then tested as provided below.

| | |
|---|---|
| Basis weight (gsm) | 30 |
| Peak Load Machine Direction (lb$_f$) | 6.46 |
| Peak Load Transversal direction (lb$_f$) | 1.2 |
| Frazier Test 6 Layers (ft$^3$/min) | 298 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A polyolefin material that is formed by drawing of a thermoplastic composition, wherein the thermoplastic composition contains a continuous phase that includes a polyolefin matrix polymer and a polymeric nanoinclusion additive and a polymeric microinclusion additive dispersed within the continuous phase in the form of discrete domains,
   wherein the polymeric nanoinclusion additive is in the form of nano-scale domains and the polymeric microinclusion additive is in the form of micro-scale domains,
   wherein the polymeric nanoinclusion additive constitutes from about 0.05 wt % to about 20 wt. % of the composition, based on the weight of the continuous phase; and
   wherein the polymeric microinclusion additive constitutes from about 1 wt % to about 20 wt % of the composition, based on the weight of the continuous phase;
   wherein a porous network is defined in the drawn thermoplastic composition that includes a plurality of micropores, and a plurality of nanopores adjacent to the nano-scale domains and/or the micro-scale domains, the nanopores having an average cross-sectional dimension of about 800 nanometers or less, the drawn thermoplastic composition having a density of about 0.90 g/cm$^3$ or less;
   wherein the polyolefin material exhibits a hydrohead value of about 50 centimeters or more and a water vapor transmission rate of about 300 g/m$^2$-24 hours or more.

2. The polyolefin material of claim 1, wherein the nanopores have an average cross-sectional dimension of from about 5 to about 700 nanometers.

3. The polyolefin material of claim 1, wherein nanopores have an average axial dimension of from about 100 to about 5000 nanometers.

4. The polyolefin material of claim 1, wherein the polyolefin matrix polymer has a melt flow rate of from about 0.5 to about 80 grams per 10 minutes as determined at a load of 2160 grams and at 230° C. in accordance with ASTM D1238.

5. The polyolefin material of claim 1, wherein the polyolefin matrix polymer is a propylene homopolymer, propylene/α-olefin copolymer, ethylene/α-olefin copolymer, or a combination thereof.

6. The polyolefin material of claim 1, wherein the polyolefin matrix polymer is a substantially isotactic polypropylene homopolymer or a copolymer containing at least about 90% by weight propylene.

7. The polyolefin material of claim 1, wherein the continuous phase constitutes from about 60 wt. % to about 99 wt. % of the thermoplastic composition.

8. The polyolefin material of claim 1, wherein the polymeric nanoinclusion additive has a nonpolar component and a polar component.

9. The polyolefin material of claim 8, wherein the polymeric nanoinclusion additive is a functionalized polyolefin.

10. The polyolefin material of claim 9, wherein the functionalized polyolefin is a polyepoxide.

11. The polyolefin material of claim 8, wherein the polymeric nanoinclusion additive has melt flow rate of from about 0.1 to about 100 grams per 10 minutes, determined at a load of 2160 grams and at a temperature at least about 40° C. above the melting temperature in accordance with ASTM D1238.

12. The polyolefin material of claim 8, wherein the ratio of the melt flow rate of the polyolefin to the melt flow rate of the polymeric nanoinclusion additive is from about 0.2 to about 8.

13. The polyolefin material of claim 1, wherein the nano-scale domains have an average cross-sectional dimension of from about 1 nanometer to about 1000 nanometers.

14. The polyolefin material of claim 1, wherein the polymeric microinclusion additive is polylactic acid.

15. The polyolefin material of claim 1, wherein the polymeric microinclusion additive has a glass transition temperature of about 0° C. or more.

16. The polyolefin material of claim 1, wherein the polymeric microinclusion additive has a melt flow rate of from about 5 to about 200 grams per 10 minutes, determined at a load of 2160 grams and at a temperature of 210° C.

17. The polyolefin material of claim 1, wherein the ratio of the melt flow rate of the polymeric microinclusion additive to the melt flow rate of the polyolefin matrix polymer is from about 0.5 to about 10.

18. The polyolefin material of claim 1, wherein the ratio of the Young's modulus elasticity of the polyolefin matrix polymer to the Young's modulus of elasticity of the polymeric microinclusion additive is from about 1 to about 250.

19. The polyolefin material of claim 1, wherein the micro-scale domains have an average axial dimension of from about 1 micrometer to about 400 micrometers.

20. The polyolefin material of claim 1, wherein the thermoplastic composition further comprises an interphase modifier.

21. The polyolefin material of claim 1, wherein the porous network is distributed in a substantially homogeneous fashion throughout the composition.

22. The polyolefin material of claim 1, wherein the nanopores are distributed in generally parallel columns.

23. The polyolefin material of claim 1, wherein the total pore volume of the polyolefin material is from about 15% to about 80%.

24. The polyolefin material of claim 1, wherein nanopores constitute about 20 vol. % or more of the total pore volume of the polyolefin material.

25. The polyolefin material of claim 1, wherein the drawn thermoplastic composition has a density of about 0.85 g/cm$^3$ or less.

26. The polyolefin material of claim 1, wherein the thermoplastic composition is generally free of blowing agents.

27. The polyolefin material of claim 1, wherein the thermoplastic composition is generally free of pore-initiating inorganic oxide fillers.

28. A method for forming a polyolefin material, the method comprising:
forming a thermoplastic composition that contains a continuous phase that includes a polyolefin matrix polymer and a polymeric nanoinclusion additive and a polymeric microinclusion additive dispersed within the continuous phase in the form of discrete domains, wherein the polymeric nanoinclusion additive is in the form of nano-scale domains and the polymeric microinclusion additive is in the form of micro-scale domains, wherein the polymeric nanoinclusion additive constitutes from about 0.05 wt % to about 20 wt. % of the composition, based on the weight of the continuous phase, and the polymeric microinclusion additive constitutes from about 1 wt % to about 20 wt % of the composition, based on the weight of the continuous phase; and solid state drawing the thermoplastic composition, wherein a porous network is defined in the drawn thermoplastic composition that includes a plurality of micropores, and a plurality of nanopores adjacent to the nano-scale domains and/or the micro-scale domains, the nanopores having an average cross-sectional dimension of about 800 nanometers or less, the drawn thermoplastic composition having a density of about 0.90 g/cm$^3$ or less;

wherein the polyolefin material exhibits a hydrohead value of about 50 centimeters or more and a water vapor transmission rate of about 300 g/m$^2$-24 hours or more.

29. The method of claim 28, wherein the thermoplastic composition is stretched to a draw ratio of from about 1.1 to about 3.0.

30. The polyolefin material of claim 1, wherein the plurality of nanopores have an aspect ratio of from about 1 to about 30.

31. The polyolefin material of claim 1, wherein the axial dimension of the micropores is greater than the cross-sectional dimension of the micropores.

* * * * *